(12) United States Patent
O'Rand

(10) Patent No.: US 10,472,334 B2
(45) Date of Patent: Nov. 12, 2019

(54) SMALL MOLECULES FOR INHIBITING MALE FERTILITY

(71) Applicant: The University of North Carolina at Chapel Hill, Chapel Hill, NC (US)

(72) Inventor: Michael O'Rand, Chapel Hill, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 221 days.

(21) Appl. No.: 15/122,528

(22) PCT Filed: Mar. 13, 2015

(86) PCT No.: PCT/US2015/020473
§ 371 (c)(1),
(2) Date: Aug. 30, 2016

(87) PCT Pub. No.: WO2015/138919
PCT Pub. Date: Sep. 17, 2015

(65) Prior Publication Data
US 2017/0057934 A1    Mar. 2, 2017

Related U.S. Application Data

(60) Provisional application No. 61/953,293, filed on Mar. 14, 2014.

(51) Int. Cl.
| | | |
|---|---|---|
| *C07D 251/52* | (2006.01) | |
| *A61K 31/53* | (2006.01) | |
| *C07D 253/07* | (2006.01) | |
| *C07D 253/075* | (2006.01) | |
| *C07D 487/04* | (2006.01) | |
| *C07D 498/04* | (2006.01) | |

(52) U.S. Cl.
CPC .......... *C07D 251/52* (2013.01); *A61K 31/53* (2013.01); *C07D 253/07* (2013.01); *C07D 253/075* (2013.01); *C07D 487/04* (2013.01); *C07D 498/04* (2013.01)

(58) Field of Classification Search
USPC ........................................ 514/245
See application file for complete search history.

(56) References Cited

U.S. PATENT DOCUMENTS

| 4,460,585 A | 7/1984 | Campbell et al. |
| 2010/0286280 A1* | 11/2010 | O'Rand ............... A61K 31/567 514/616 |

FOREIGN PATENT DOCUMENTS

| CN | 101402674 A | 8/2009 |
| WO | 2001085700 A2 | 11/2001 |
| WO | 2009042565 A2 | 4/2009 |

OTHER PUBLICATIONS

International Search Report for PCT Application No. PCT/US2015/020473 dated Jul. 23, 2015.

* cited by examiner

*Primary Examiner* — Kathrien A Cruz
(74) *Attorney, Agent, or Firm* — Nexsen Pruet PLLC; David Bradin

(57) ABSTRACT

Compounds suitable for use in providing male contraception, an assay method for identifying such compounds, and methods of providing contraception using the compounds, are provided. In one embodiment, the compounds described herein mimic the binding of anti-EPPIN antibodies to EPPIN, and thus inhibit the forward motility of sperm in humans and other primates. In another embodiment, the compounds described herein inhibit or enhance EPPIN-semenogelin binding, and inhibit forward motility of sperm. The assays described herein identify compounds which inhibit sperm motility, and can be carried out in a high throughput manner, using labeled recombinant EPPIN and semenogelin. The compounds can be used in oral or transdermal compositions to temporarily and reversibly inhibit male fertility. They can also be used in addition to, or in place of, spermicides in spermicidal compositions, such as those used in conjunction with condoms, diaphragms, and spermicidal jellies.

14 Claims, 10 Drawing Sheets

Specification includes a Sequence Listing.

| | |
|---|---|
| Name | [4-(3-hydroxy-4-methoxycarbonylamino-phenylamino)-6-(N'-methoxycarbonyl-hydrazino)-1,3,5-triazin-2-ylsulfanyl]-acetic acid ethyl ester |
| Use | For research and development only |
| Lot No. | 336PAL39 |
| Molecular Formula | $C_{17}H_{21}N_7O_7S$ |
| Structure | |

| Manufacturing Date | 06/10/13 | Storage | Storage in Freezer |
|---|---|---|---|
| Analysis - Results | | By | Date |
| Appearance | | XJ | 07/01/13 |
| MS | | XJ | 06/13/13 |
| HPLC | | XJ | 06/13/13 |
| $^1$H NMR | | XJ | 07/01/13 |
| Analysis - Conditions | | | |
| MS | Electrospray Positive Mode | | |
| HPLC | Column: Restek Pinnacle II, C18, 5µ, 150 X 4.6 mm. Gradient/MP: 5% to 100% over 30 min. Total run time: 30 min. MeOH in $H_2O$ + 0.1 % TFA. Flow: 1.5 mL/min.. Detector: 254 nm (VWD) | | |
| NMR | Proton: 400 MHz, $CD_3OD$ | | |

Figure 1

| Incubation (minutes) | 10 μM TZ4_121_L4 | 20 μM TZ4_121_L4 | DMSO |
|---|---|---|---|
| 0.100 | 1.28 | 0.85 | 1.00 |
| 5.000 | 1.31 | 0.27 | 1.00 |
| 15.000 | 1.03 | 0.27 | 1.00 |
| 30.000 | 0.72 | 0.11 | 1.00 |
| 60.000 | 0.62 | 0.00 | 1.00 |
| 120.000 | 0.53 | 0.00 | 1.00 |

SMALL MOLECULES FOR INHIBITING MALE FERTILITY

CROSS-REFERENCE TO RELATED APPLICATIONS

This application claims priority under 35 U.S.C. 371 to PCT WO 2015/138919, filed on Mar. 13, 2015, which in turn claims priority to U.S. Provisional Application Ser. No. 61/953,293, filed on Mar. 14, 2014. The contents of each of these applications is incorporated by reference in their entirety for all purposes.

BACKGROUND OF THE INVENTION

Over the last 50 years, contraception has had a major impact on human society and influenced the worldwide distribution of family sizes and the variability of fertility rates (Bongaarts and Watkins, 1996; Bongaarts, 1997). This impact can be largely attributed to female contraceptive methods, their availability and economic and social costs.

Male contraception, on the other hand, has had much less of a global impact, being largely limited to condoms and vasectomy (Nass and Strauss, 2004). Female hormonal contraceptives work through the mechanism of anovulation and the goal of male hormonal contraceptive research is analogous, namely the suppression of spermatogenesis to produce azoospermia. However, achievement of this goal in a reliable way for a diverse population of men is still many years away (Grimes et al., 2005; Potts, 1996).

Even further away is the dream of a non-hormonal male contraceptive in which it may be envisioned that spermatozoa do not develop, or do not swim, or do not fertilize or some combination of these spermatozoan catastrophes. Numerous contraceptive targets abound and several of these targets are worthy of further exploratory work, including blocking transmembrane ion currents (Kirichok et al., 2006; Brenton et al., 1996), disrupting Sertoli-germ cell adhesions (Cheng et al., 2002, 2005) and disruption of spermiogenesis by imino sugars (Walden et al., 2006).

Immunocontraception, which showed great promise for many years, has lost its appeal. Nevertheless, immunocontraception can be used as a strategy to discern the function of target molecules in the male. As an example, EPPIN is an epididymal protease inhibitor that coats the surface of human spermatozoa. EPPIN modulates PSA (prostate specific antigen, a serine protease) activity and the hydrolysis of semenogelin. Although EPPIN modulates the hydrolysis of semenogelin by PSA, antibodies to EPPIN do not inhibit PSA activity.

Ejaculate spermatozoa of monkeys and humans are coated with EPPIN. On the surface of spermatozoa EPPIN binds the protein semenogelin, which is secreted by the seminal vesicles during ejaculation. The EPPIN-semenogelin complex is removed during liquefaction of semen during the first 30 minutes after ejaculation. Failure to remove semenogelin results in infertile spermatozoa. Studies of the interaction of EPPIN and semenogelin, and their effect on human spermatozoa, are described, for example, in Wang, Z., Widgren, E. E., Sivashanmugam, P., O'Rand, M. G., and Richardson, R. T. 2005. Association of EPPIN with semenogelin on human spermatozoa, Biology of Reproduction 72 (4): 1064-1070 (Dec. 8, 2004).

One strategy for developing new contraceptives is to immunize primates with specific sperm surface antigens and determine the effects of the immune response on the ejaculated spermatozoa of immunized males. Recent work on EPPIN, (SPINLW1; serine protease inhibitor-like, with Kunitz and WAP domains-1) provides an example of the utility of the immunocontraceptive approach (O'Rand et al., 2004; Wang et al., 2005; O'Rand et al., 2006). A fertility study (O'Rand et al., 2004) demonstrated that effective and reversible male immunocontraception in primates is an obtainable goal. A high serum titer (>1:1000) sustained over several months achieved an effective level of contraception. Treatment of human spermatozoa with antibodies to EPPIN derived from primates showed a decrease in motility of the treated spermatozoa, (results are described, for example, in O'Rand, M. G., Widgren, E. E., Beyler, S. and Richardson, R. T. 2009. Inhibition of human sperm motility by contraceptive anti-EPPIN antibodies from infertile male monkeys: effect on cyclic adenosine monophosphate, Biology of Reproduction 80: 279-285 (Oct. 22, 2008).

The data were obtained from the analysis of affinity purified anti-EPPIN antibodies. Compared to control, there was a significant difference in the progressive motility of human sperm after treatment with anti-EPPIN antibodies as judged by a decrease in the total distance traveled by 71% ($p<6.26\times10^{-10}$) and the straight line distance by 57% ($p<5.37\times10^{-25}$), while the velocity decreased by 71% ($p<3.96\times10^{-8}$). At the same time the antibodies had the effect of increasing the bend angle between the straight-line vector (distance) and a turn, i.e. the back and forth movement of the head (tortuosity).

Consequently, in addition to whatever conclusions one may wish to draw about the feasibility of using immunocontraception, one can conclude from these studies that EPPIN has an essential role in fertility.

Antibodies are prone to degradation in the stomach if orally administered, and for this reason, are commonly administered by injection. Because it is unlikely that male contraception will be viable if it requires routine injections, it would be advantageous to have small molecules that also bind EPPIN and inhibit anti-EPPIN or semenogelin binding. The present invention provides such compounds, an assay for identifying such compounds, and methods for their use.

SUMMARY OF THE INVENTION

Compounds suitable for use in providing male contraception by inhibiting the forward motility of sperm in humans and other primates, methods of identifying such compounds, and methods of providing contraception using the compounds are provided.

The development of a non-hormonal male contraceptive can enhance family planning throughout the world and give men and women additional contraceptive choices. Currently men are limited in their options for contraception to condoms and vasectomy. In recent surveys, the satisfaction rate for women on contraception is less than 60% for every method except tubal ligation and men want access to better contraceptives. Therefore a non-hormonal male contraceptive will fill an unmet need in contraception.

EPPIN (SPINLW1; epididymal protease inhibitor) coats the surface of human testicular, epididymal and ejaculate spermatozoa in an EPPIN protein complex (EPC) containing lactotransferrin and clusterin. EPPIN is a target for the assays described herein.

During ejaculation, semenogelin (SEMG1) binds to EPPIN in the complex, inhibiting the progressive motility of ejaculate spermatozoa. The EPPIN-semenogelin complex is on the surface of sperm. Subsequently, SEMG1 is hydrolyzed by the serine protease PSA and EPPIN modulates PSA hydrolysis of SEMG1 on the sperm surface, resulting in forwardly motile spermatozoa.

Previous studies on the antisera from the infertile monkeys revealed 2 linear B-cell epitopes of anti-EPPIN, one in the N-terminal and one in the C-terminal. The C-terminal epitope was identified as TCSMFVYGGCQGNNNNFQ-KANCLN (SEQ ID NO. 1). Antibodies to this epitope inhibit sperm motility and semenogelin binding.

Immunocontraception (i.e., the use of antibodies to bring about contraception) is not considered a viable option for a marketable product for efficacy, safety, and economic reasons. Accordingly, in one embodiment, the invention relates to small organic compounds that mimic anti-EPPIN antibody (i.e. compounds that bind EPPIN in the same position or substantially the same position as anti-EPPIN antibodies, and thus act as small molecule mimics for these antibodies), and thus inhibit the forward motility of sperm, methods for their identification, and methods for their use in providing male contraception. These compounds can be administered orally, for example, and taken on-demand a relatively short time before ejaculation.

Based on a publication in Science in 2004, demonstrating the "proof of principle" that blocking EPPIN-SEMG1 interaction results in the complete and reversible contraception of male monkeys immunized to a high titer with EPPIN, small organic lead compounds were developed as a sperm contraceptive. Accordingly, in one embodiment, the compounds inhibit semenogelin binding to EPPIN. Small organic compounds that inhibit sperm motility by fitting into the EPPIN-SEMG1 binding site on the surface of spermatozoa can be administered orally, and taken on-demand a relatively short time before ejaculation.

In this embodiment, useful compounds include those that a) bind to the binding site on EPPIN for semenogelin (also referred to herein as Sg), or which bind to an allosteric position in a manner which inhibits semenogelin from binding, and which also mimic the effect of the semenogelin, namely to stop sperm from swimming. Ideally, those compounds which interfere with EPPIN semenogelin binding bind with higher affinity to the active binding pocket than semenogelin. This will enable one to administer lower effective concentrations of the compounds than compounds that bind with lower binding affinity. Those compounds which bind in an allosteric manner are also, ideally, high affinity compounds, so that lower effective concentrations of these compounds can be administered as well.

In addition to the compounds described herein, assays are also described herein, which assays identify compounds which inhibit the forward motility of sperm. In one embodiment, the compounds bind to the same position as anti-EPPIN antibodies, and thus act as small molecule mimics for these antibodies. In another embodiment, the compounds inhibit sperm motility by inhibiting EPPIN-semenogelin binding.

Two assays for high throughput screening (HTS) of compounds have been established and validated. In one embodiment, these assays are based on an adaptation of the AlphaScreen™ assay developed by PerkinElmer (Waltham, Mass.). In the AlphaScreen™ (amplified luminescent proximity homogeneous assay) assay donor and acceptor beads (~200 nm) are employed to hold interacting protein molecules. When the interacting protein molecules bind (for example EPPIN {on the donor bead} and anti-EPPIN {on the acceptor bead}), singlet state oxygen molecules diffuse from the donor bead to the acceptor bead (~4 µsec) and fluorophores subsequently emit light at 520-620 nm. In the primary compound screen, histidine-tagged recombinant human EPPIN is attached to NTA-donor beads and anti-EPPIN (S21C; against the EPPIN C-terminal domain) is attached to protein A-acceptor beads. This epitope specific assay gives strong and stable binding between EPPIN and the antibody.

In one aspect of this embodiment, for a secondary compound screen, donor beads that bind biotinylated SEMG1 and acceptor beads that bind EPPIN via anti-EPPIN (N-terminal) antibodies and protein A-acceptor beads can be used. This assay allows SEMG1 to bind to its EPPIN binding site on the EPPIN C-terminal. In another aspect of this embodiment, for a control compound screen, a Modified TruHits Assay for non-specific bead binding can be used.

Once the activity of the compounds is determined, it can also be important to determine other pharmacological properties, including adsorption, distribution, metabolism, excretion, and toxicology. Any of a number of known screening assays can be used for this purpose. For example, a cytotoxicity assay called CellTiter-Glo®, a Luminescent Cell Viability Assay from Promega Corporation that is an automated high-throughput screen for cell proliferation and cytotoxicity can be used to determine the toxicity of the compounds.

In another embodiment, a computer-assisted sperm analysis (CASA) can be used as a live cell compound screen for determining the effect of compounds on human sperm motility. Additionally, to facilitate the $IC_{50}$ evaluation of compounds using different ejaculates, reducing inter-assay variation due to differences in sperm quality in different semen samples, an index of relative motility inhibition (RMI) was developed.

This is calculated as: RMI=[% motility*VSL]; percentage of motile sperm (% motility) or the percentage of progressively motile sperm (% progressive motility, RPMI) multiplied by the straight-line velocity (VSL); the average velocity measured in a straight line from the beginning to the end of a track in µm/sec.

Normalized RMI can be calculated by dividing the RMI of each experimental condition by its respective DMSO control.

Using the assays described above, over 100,000 compounds were screened. Data from the screens enabled structural clusters of lead compounds to be identified. One cluster of active compounds is described herein as being Series TZ4. Series TZ4 are compounds with a 1,3,5 triazine ring. The TZ4 lead compound family was developed from the initial screening rounds of other series. Based on compound docking studies, using the EPPIN C-terminal binding site for SEMG1, the lead compounds have been synthesized.

In vivo, the contraceptive drug must bind to EPPIN in the epididymis and either binds to the site at which the anti-EPPIN antibodies would bind, compete with semenogelin (SEMG1) for binding to EPPIN on the surface of sperm during ejaculation, or enhance the binding of semenogelin to EPPIN. The calculated $EC_{50}$ value for SEMG1 inhibiting sperm motility is 8.8 µM. Active compounds ideally have an $EC_{50}$ value within an order of magnitude of this $EC_{50}$ value, though compounds with higher and lower EC50 values can be useful, so long as they can be safely administered at effective dosages.

Of the TZ4 lead compound family, TZ4_121 ([4-(3-Hydroxy-4-methoxycarbonylamino-phenylamino)-6-(N'm-ethoxycarbonyl-hydrazino)-1,3,5-triazin-2-ylsulfanyl]-acetic acid ethyl ester] and 2. [2-Amino-5-[4-ethoxycarbonyl-methylsulfanyl-6-(N'-methoxycarbonyl-hydrazino)[1,3,5] triazin-2-ylamino]-benzoic acid methyl ester]) has a CASA $IC_{50}$ RPMI of 7.5 µM. TZ4_121 can kill >70% of the sperm within 3 minutes. It is expected that the effect on motility in vivo will be identical to that of SEMG1.

Lipinski's rule of five is a rule of thumb to evaluate whether a compound has properties that would make it a likely orally active drug in humans. The rule describes molecular properties important for a drug's pharmacokinetics in the human body, including their absorption, distribution, metabolism, and excretion ("ADME"). According to this rule, a compound should have no more than five hydrogen bond donors (the total number of nitrogen-hydrogen and oxygen-hydrogen bonds), not more than ten hydrogen bond acceptors (all nitrogen or oxygen atoms), a molecular mass less than 500 Daltons, and an octanol-water partition coefficient log P not greater than five. Among the compounds described herein, the most active compound, TZ4_121 (except for an additional hydrogen bond acceptor), does not violate the rule. Accordingly, it is believed that the compounds described herein will be orally bioavailable.

In addition to compounds that mimic the anti-EPPIN antibodies, it has been found that certain compounds bind EPPIN in the same site as semenogelin (as opposed to an allosteric position), and bind more tightly than semenogelin, thus inhibiting formation of an EPPIN-semenogelin complex. Other compounds bind EPPIN in an allosteric position, and inhibit EPPIN-semenogelin complex formation in that manner. Still other compounds enhance EPPIN-semenogelin complex formation. Any of these embodiments will work to inhibit spermatozoa forward motility.

Compounds that mimic the binding of an anti-EPPIN antibody to EPPIN, or which inhibit semenogelin from binding to EPPIN, and thus inhibit spermatozoa forward motility, can be used to temporarily and reversibly cause male infertility.

The compounds can be included in compositions, which ideally are oral or transdermal compositions, which release an appropriate amount of the compounds to produce this effect. For example, the compounds can be used in once-daily tablets or pills, or transdermal patches for periods of time longer than a day, much in the same manner as female contraceptives.

In another embodiment, the compounds can be used in addition to, or in place of, spermicides in spermicidal compositions, such as those used in conjunction with condoms, diaphragms, and spermicidal jellies. That is, since the compounds can function on contact with spermatozoa to inhibit forward motility, it is not necessary that they be ingested to have the effect.

Thus, the invention described herein provides an advantage over the prior art, in that the user has a choice of male contraception between in vivo activity of the compounds to inhibit the forward motility of spermatozoa before ejaculation, or use of the compound after ejaculation to inhibit forward motility of the spermatozoa.

The present invention will be better understood with reference to the following detailed description.

BRIEF DESCRIPTION OF THE FIGURES

FIG. 1 is a chart showing analytical results for compound TZ4_121.

DETAILED DESCRIPTION

Figure 2:
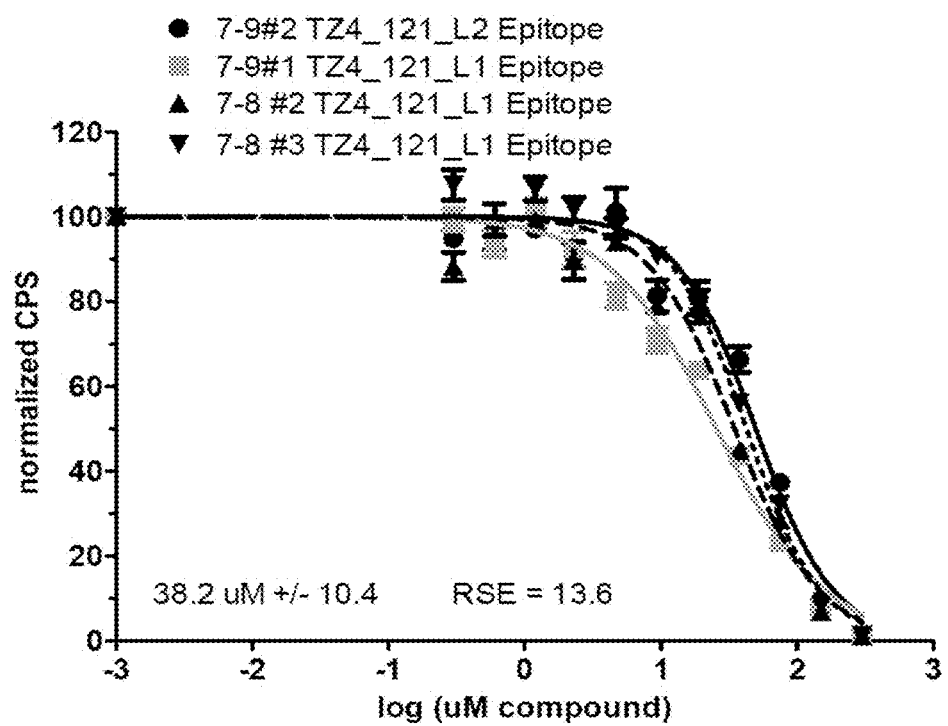
FIG. 2 is a chart showing the $IC_{50}$ value for compound TZ4_121. The data is shown in terms of percent of control value vs. Log of TZ4_121 concentration.

Compounds suitable for use in providing male contraception, an assay method for identifying such compounds, and methods of providing contraception using the compounds, are provided.

The male contraceptive target EPPIN controls sperm motility in the ejaculate by binding semenogelin (SEMG1), which lowers sperm pH, resulting in a loss of intracellular calcium, and a loss of sperm motility. Anti-EPPIN antibodies substitute for SEMG1 and have a similar effect. Described herein are small molecular weight compounds that mimic anti-EPPIN binding, which substitute for SEMG1, and provide non-antibody, non-hormonal male contraceptives. Also described herein is an assay for identifying such compounds, and methods for using the compounds as contraceptives.

The present invention will be better understood with reference to the following definitions.

Definitions

EPPIN (SPINLW1; serine protease inhibitor-like, with Kunitz and WAP domains 1) is a member of the whey acidic protein (WAP)-type four-disulfide core (WFDC) gene family. The WFDC genes are on human chromosome 20q12-q13 in two clusters, one centromeric and one telomeric (Clauss et al., 2002). EPPIN is WFDC 7 in the telomeric cluster and is the archetype of WFDC genes characterized by encoding both Kunitz-type and WAP-type four disulfide core protease inhibitor consensus sequences (Richardson et al., 2001).

EPPIN is a testis/epididymal specific protein (Richardson et al., Gene 270, 93 (2001) and Sivashanmugam, et al., Gene 312, 125 (2003). The human EPPIN gene on chromosome 20 encodes two isoforms, one with and one without a secretory signal sequence, each containing both a Kunitz-type and a WAP-type (four-disulfide core) protease inhibitor consensus sequence. EPPIN represents the first member of a family of protease inhibitors on human chromosome 20 characterized by dual inhibitor consensus sequences (ibid). There are three splice variants of EPPIN that are expressed differently; EPPIN-1 is expressed in the testis and epididymis, EPPIN-2 is expressed in the epididymis and EPPIN-3 in the testis.

The preparation of recombinant human EPPIN (rhEPPIN) has been described in detail (Wang et al., Biology of Reproduction, 72:1064-1070 (2005) and the rhEPPIN used in the examples described herein lacks part of the N-terminal secretory signal sequence as described in Wang et., ibid. Briefly, rhEPPIN was prepared in *E. coli* strain M15 [pREP-4] and the protein purified from the bacterial lysate on a $Ni^{2+}$-NTA column (Qiagen, Valencia, Calif.; 21). Purified rhEPPIN was extensively dialyzed against phosphate buffered saline (PBS, pH 7.2) before use. The recombinant EPPIN used in the assays described herein has been tagged with a FLAG tag.

Semenogelin I (SgI) and semenogelin II (SgII) are the dominating protein components of the coagulum formed by freshly ejaculated human semen. These proteins are primarily found in the seminal vesicles, although SgII is produced in small amounts in the epididymis. These proteins have not been detected in other tissues Lundwall et al., Mol. Hum. Reprod. 8(9):805-10 (September 2002).

Semenogelin-1 has the following sequence:

```
                                         (SEQ ID NO. 2)
MKPNIIFVLS  LLLILEKQAA  VMGQKGGSKG  RLPSEFSQFP

HGQKGQHYSG  QKGKQQTESK  GSFSIQYTYH  VDANDHDQSR

KSQQYDLNAL  HKTTKSQRHL  GGSQQLLHNK  QEGRDHDKSK

GHFHRVVIHH  KGGKAHRGTQ  NPSQDQGNSP  SGKGISSQYS

NTEERLWVHG  LSKEQTSVSG  AQKGRKQGGS  QSSYVLQTEE

LVANKQQRET  KNSHQNKGHY  QNVVEVREEH  SSKVQTSLCP

AHQDKLQHGS  DIFSTQDEL  LVYNKNQHQT  KNLNQDQQHG

RKANKISYQS  SSTEERRLHY  GENGVQKDVS  QSSIYSQTEE

KAQGKSQKQI  TIPSQEQEHS  QKANKISYQS  SSTEERRLHY

GENGVQKDVS  QRSIYSQTEK  LVAGKSQIQA  PNPKQEPWHG

ENAKGESGQS  TNREQDLLSH  EQKGRHQHGS  HGGLDIVIIE

QEDDSDRHLA  QHLNNDRNPL  FT
```

(French K C, Roan N R and Makhatadze G I, "Structural characterization of semen coagulum-derived SEM1(86-107) amyloid fibrils that enhance HIV-1 infection," *Biochemistry*, 53 (20), 3267-3277 (2014)).

Recombinant semenogelin, as used herein, is a His-tagged recombinant protein, such as that described in Wang et al., Biology of Reproduction, 72:1064-1070 (2005), the contents of which are hereby incorporated by reference, which first described EPPIN-semenogelin binding. In this paper, two recombinant fragments of semenogelin are described, which were identified via polymerase chain reaction (PCR). The fragment starting with amino acid 164 and extending to amino acid 283 binds to EPPIN. This fragment can be appropriately His-tagged and used in the assays described herein.

The terms "active ingredient" or "active agent" mean compounds which inhibit EPPIN-semenogelin binding and inhibit spermatozoa forward motility, as well as any prodrugs thereof and pharmaceutically acceptable salts, hydrates, and solvates of the compound and the prodrugs. The term "other ingredients" means any excipients, diluents, binders, lubricants, carriers, surfactants, and mixtures thereof that are formulated with the active compounds described herein, or any prodrugs thereof, and pharmaceutically acceptable salts, hydrates, and solvates thereof.

The term "appropriate period of time" or "suitable period of time" means the period of time necessary to achieve a desired effect or result. For example, a mixture can be blended until a potency distribution is reached that is within an acceptable range for a given application or use of the blended mixture.

"Carriers" or "vehicles" as used herein refer to carrier materials suitable for drug administration, specifically including oral and transdermal administration, and include any such materials known in the art, e.g., any liquid, gel, solvent, liquid diluent, solubilizer, or the like, which is non-toxic and which does not interact with other components of the composition in a deleterious manner. Examples of suitable vehicles for use in transdermal formulations include water, alcohols such as isopropyl alcohol and isobutyl alcohol, polyalcohols such as glycerol, and glycols such as propylene glycol, and esters of such polyols, (e.g., mono-, di-, or tri-glycerides).

By "controlled" is meant reduced or minimized peak and valley exposure cycles in blood, plasma, or other biological fluids normally present in some routes of administration of a pharmacologically active agent.

An "effective" or an "adequate" permeation enhancer for transdermal formulations as used herein means a permeation enhancer that will provide the desired increase in skin permeability and correspondingly, the desired depth of penetration, rate of administration, and amount of drug delivered.

The term "effective amount," as used herein means the amount determined by such considerations as are known in the art for causing temporary and reversible male contraception.

"Penetration enhancement" or "permeation enhancement" as used herein in connection with transdermal administration relates to an increase in the permeability of skin to a pharmacologically active agent, i.e., so as to increase the rate at which the drug permeates through the skin (i.e., flux) and enters the bloodstream. The enhanced permeation effected by using these enhancers can be observed by measuring the rate of diffusion (or flux) of drug through animal or human skin or a suitable polymeric membrane using a diffusion cell apparatus as described in the examples herein.

By "transdermal" delivery, applicants intend to include both transdermal (or "percutaneous") and transmucosal administration, i.e., delivery by passage of a drug through the skin or mucosal tissue and into the bloodstream.

By "sustained" is meant extended maintenance of steady state plasma levels of an active compound.

The term "unit dose," "unit dosage," or "unit dosage form" means a physically discrete unit that contains a predetermined quantity of active ingredient calculated to produce a desired therapeutic effect. The dosage form can be in any suitable form for administration, such as oral or transdermal administration, which forms are well known to those of skill in the art.

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. Specifically included are $CH_2F$ and $CHF_2$.

In the text, whenever the term C(alkyl range) is used, the term independently includes each member of that class as if specifically and separately set out. The term "alkyl" includes $C_{1-6}$ alkyl moieties. It is understood to those of ordinary skill in the art that the relevant alkyl radical is named by replacing the suffix "-ane" with the suffix "-yl".

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2 propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moeities. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties.

The aryl group can be optionally substituted with any moiety that does not adversely affect the compound synthesis, including but not limited to those described above for alkyl moieties.

In one embodiment, aryl groups also include $C_{5-10}$ heteroaryl rings, such as thiophene, pyrollidine, pyridine, and pyrimidine, which can be substituted in the same manner as the carbocyclic aryl rings.

The terms "alkaryl" or "alkylaryl" refer to an alkyl group with an aryl substituent. The terms "aralkyl" or "arylalkyl" refer to an aryl group with an alkyl substituent. More specifically, alkyl-aryl is a $C_{1-6}$ alkyl group bound to a $C_{5-10}$ aryl or heteroaryl ring, such as a benzyl group, and aryl-alkyl is a $C_{5-10}$ aryl or heteroaryl ring bound to a $C_{1-6}$ alkyl group.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including but not limited to methoxymethyl, aralkyl including but not limited to benzyl, aryloxyalkyl such as phenoxymethyl, aryl including but not limited to phenyl optionally substituted with halogen (F, Cl, Br, I), alkyl (including but not limited to C1, C2, C3, and C4) or alkoxy (including but not limited to C1, C2, C3, and C4), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

In some embodiments, the active compounds are present in the form of amines, and their pharmaceutically acceptable salts. Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, benzoate, and ascorbate; salts with amino acids such as lysine monohydrochloride, aspartate and glutamate. The salts may be in some cases hydrates or ethanol solvates. The salts can be prepared by reacting an active compound as described herein with a suitable acid. For transdermal administration, it can be preferred that the acid is a fatty acid, to form a salt that has relatively easy transmission through the skin.

In any embodiment described herein, the active blend of a dosage form generally includes one or more pharmaceutically acceptable adhesives, excipients, carriers, diluents, binders, lubricants, glidants, or disintegrants and depends upon the purpose for which the active ingredient is being applied. In general, transdermal formulations are made of other ingredients including, but not limited to, excipients, diluents, carriers, permeation enhancers, and mixtures thereof.

I. Compounds

In some embodiments, the compounds described herein do not inhibit EPPIN-semenogelin binding, per se, but rather, bind to that portion of EPPIN to which anti-EPPIN antibodies bind. Representative anti-EPPIN antibodies are disclosed in O'Rand et al., Biology of Reproduction, 80, 279-285 (2009).

In other embodiments, the compounds described herein inhibit or enhance EPPIN-semenogelin binding, and inhibit forward motility of sperm in humans and other primates. The EPPIN-semenogelin complex is on the surface of sperm. Useful compounds include those that a) bind to the binding site on EPPIN for semenogelin (also referred to herein as Sg), b) bind to an allosteric position in a manner which inhibits semenogelin from binding, and which also mimic the effect of the semenogelin, namely to stop sperm from swimming, and c) enhance the binding of semenogelin to EPPIN.

Ideally, those compounds which mimic the binding of the anti-EPPIN antibodies bind with higher affinity than the antibodies themselves, and/or those compounds which interfere with EPPIN semenogelin binding bind with higher affinity to the active binding pocket than semenogelin. This will enable one to administer lower effective concentrations of the compounds than compounds that bind with lower binding affinity. Those compounds which bind in an allosteric manner are also, ideally, high affinity compounds, so that lower effective concentrations of these compounds can be administered as well.

Compounds identified in the high-throughput assay as mimicking the binding of the anti-EPPIN antibodies, or inhibiting the binding of EPPIN and semenogelin, and also identified as having a negative impact on spermatozoa motility, can be used in the methods described herein.

In one embodiment, the compounds described herein generally have one of the following formulas:

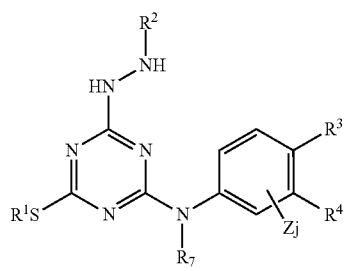

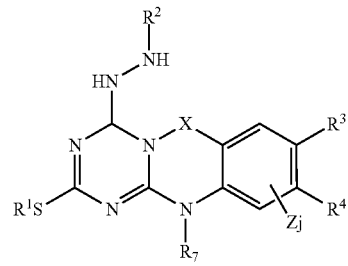

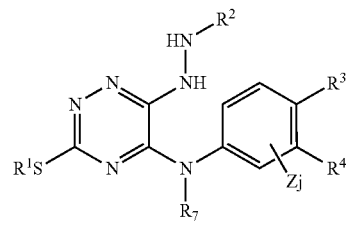

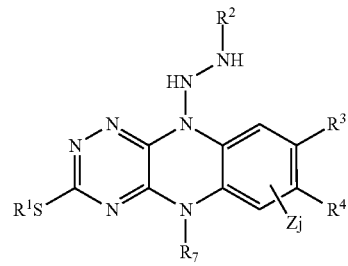

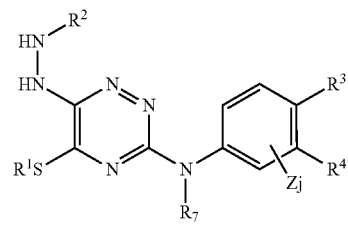

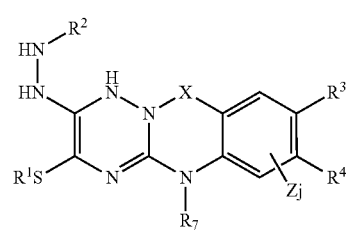

and tautomers, prodrugs, and pharmaceutically-acceptable salts thereof, wherein:

$R^1$ is —$CH_2R^5$, $R^2$ is H, $C_{1-8}$ alkyl, $C_{1-8}$ haloalkyl, $C_{2-8}$ alkenyl, $C_{2-8}$ alkynyl, aryl, arylalkyl, alkylaryl, C(X)$R^6$ or C(X)X$R^6$, $R^3$ is —NH$R^7$, —C(X)NH$R^7$, —NHC(X)$R^7$, —NHC(X) X$R^7$, —$R^8$, or —C(X)$R^8$;

$R^4$ is O$R^7$ or —C(X)O$R^7$, $R^5$ is H, F, $C_{1-8}$ alkyl, $C_{1-8}$ haloalkyl, $C_{2-8}$ alkenyl, $C_{2-8}$ alkynyl, aryl, arylalkyl, alkylaryl, —XC(X)X$R^6$, C(X)X$R^6$, or C(X)$R^6$, $R^6$ and $R^7$ are H, $C_{1-8}$ alkyl, $C_{1-8}$ haloalkyl, $C_{2-8}$ alkenyl, $C_{2-8}$ alkynyl, aryl, arylalkyl, or alkylaryl;

$R^8$ is

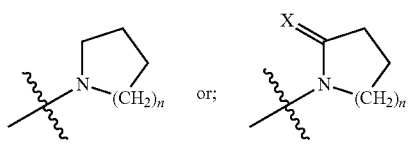

X is O, S, or $NR^7$, and is preferably O,

Y is O, S, $NR^7$, or $C(R^7)_2$,

Zj refers to j number of Z substituents, which substituents can be present at any carbon atom on the benzene ring, wherein j is 0, 1 or 2, each Z is, individually, a substituent species selected from the group consisting of $C_{1-8}$ alkyl, $C_{1-8}$ substituted alkyl, $C_{2-8}$ alkenyl, $C_{2-8}$ substituted alkenyl, heterocyclyl, substituted heterocyclyl, $C_{3-8}$ cycloalkyl, $C_{3-8}$ substituted cycloalkyl, aryl (including heteroaryl), substituted aryl (including heteroaryl), alkylaryl, substituted alkylaryl, arylalkyl, substituted arylalkyl, halo (e.g., F, Cl, Br, or I), —$OR^7$, —$N(R^7)_2$, —$CF_3$, —CN, —$NO_2$, —$C_2R^7$, —$SR^7$, —$N_3$, —C(=O)N$(R^7)_2$, —$NR^7$C(=O)$R^7$, —C(=O)$R^7$, —C(=O)$OR^7$, —OC(=O)$R^7$, —O$(CR^6R^7)_r$C(=O)$R^7$—, —O$(CR^6R^7)_r$N$R^7$C(=O)$R^7$, —O$(CR^6R^7)_r$N$R^7$SO$_2R^7$, —OC(=O)N$R^6R^7$, —$NR^7$C(=O)$OR^7$, —SO$_2R^7$, —SO$_2NR^6R^7$, and —$NR^7$SO$_2R^7$, r is an integer from 1 to 6, and n is 0, 1, 2, or 3.

the term "substituted" as applied to alkyl, aryl (including heteroaryl), cycloalkyl and the like refers to the substituents described above, starting with halo and ending with —$NR^7$SO$_2R^7$; and wherein the compounds can exist as single stereoisomers or as mixtures of stereoisomers.

A preferred haloalkyl is a mono-fluoroalkyl, such as fluoromethyl.

In terms of preferred structures, the two types of heteroaryl rings shown in the above formulas each include three ring nitrogens. When in silico and/or in vitro analyses were performed, compounds with zero, one, or two ring nitrogens did not work well. For this reason, each of the formulas provided above includes three ring nitrogens.

When $R^5$ is H, the compounds are not as active as when $R^5$ is F, —XC(X)$XR_6$, or C(X)$XR_6$.

In one embodiment, one or more C=X moieties are carbonyl (C=O). In one aspect of this embodiment, all of the C=X moieties are C=O.

Where C(X)$XR_6$ is an ester (i.e., where both of the X variables are O), the ester can be one which is easily hydrolyzed in vivo to form a carboxylic acid, or can be resistant to in vivo hydrolysis, such as a t-butyl ester. The same applies to carbamates and carbonates.

When a $C_{1-8}$ haloalkyl moiety is present, and is a fluoromethyl group, it has been generally observed that one fluorine works well, two fluorines work fairly well, but not as well as when only one fluorine is present, and trifluoromethyl does not appear to work well, as it appears to push the compound out of the pocket. That said, the presence of a single fluorine, or two fluorines, appears advantageous. On information and belief, the fluorine atom hinders the rate at which the compounds are hydrolyzed.

Representative compounds are provided below:

TZ4_121 (EP007)

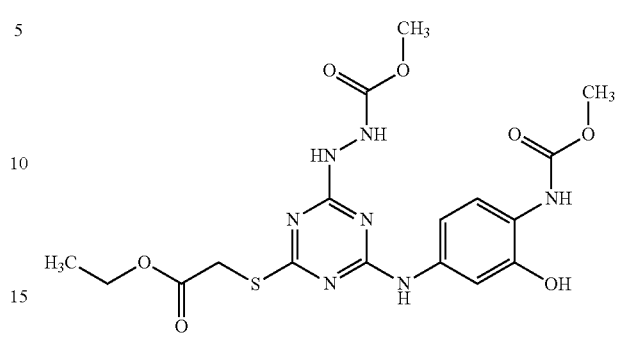

EP012 deethylated product of TZ4_121

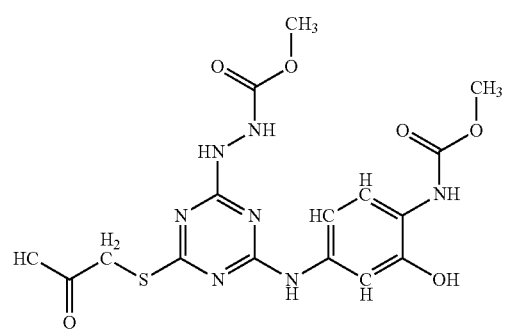 [SMILES: COC(=O)NNc1nc(Nc2ccc(NC(=O)OC)c(O)c2)nc(SCC(C)=O)n1]

TZ4_125

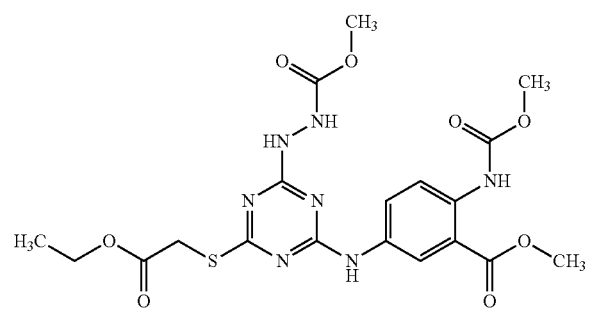 [SMILES: CCOC(=O)CSc1nc(NNC(=O)OC)nc(Nc2ccc(NC(=O)OC)c(C(=O)OC)c2)n1]

EP013 deethylated product of TZ4_125

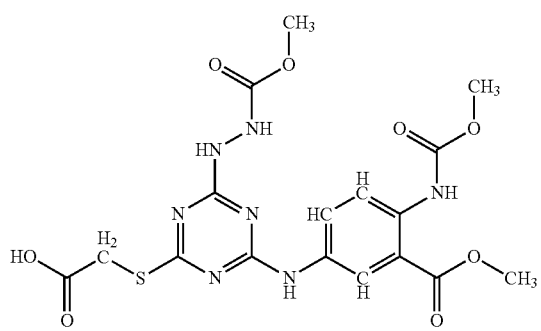 [SMILES: COC(=O)NNc1nc(Nc2ccc(NC(=O)OC)c(C(=O)OC)c2)nc(SCC(=O)O)n1]

TZ4_132

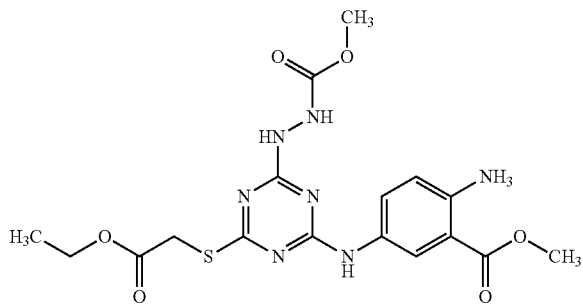 [SMILES: CCOC(=O)CSc1nc(NNC(=O)OC)nc(Nc2ccc(N)c(C(=O)OC)c2)n1]

EP025 deethylated product of TZ4_132

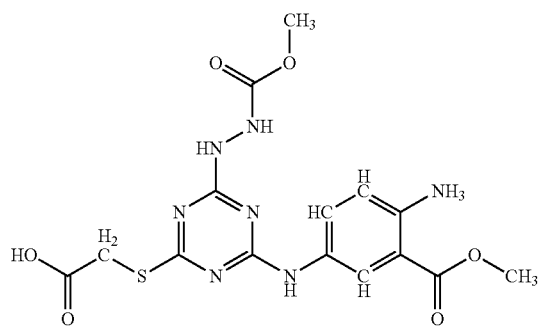 [SMILES: COC(=O)NNc1nc(Nc2ccc(N)c(C(=O)OC)c2)nc(SCC(=O)O)n1]

Closed ring structures
EP017 (from EP012)

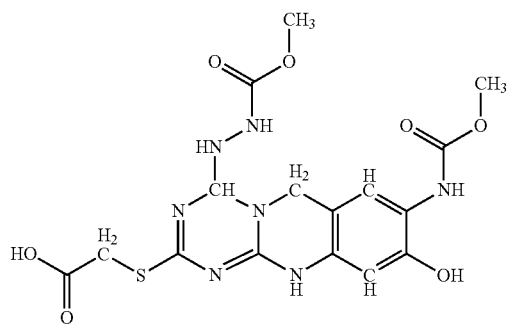 [SMILES: COC(=O)NNC1N=C(SCC(=O)O)N=C2Nc3cc(O)c(NC(=O)OC)cc3CN21]

EP021 (from EP012)

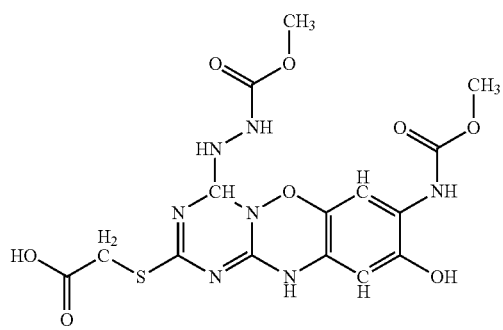 [SMILES: COC(=O)NNC1N=C(SCC(=O)O)N=C2Nc3cc(O)c(NC(=O)OC)cc3ON21]

EP024 (from EP012)

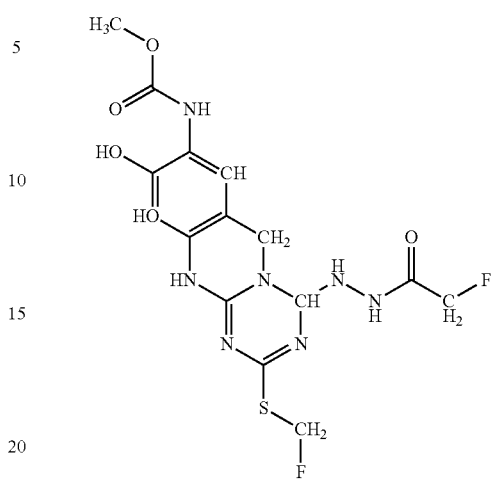

Those compounds where $R^1$ includes an ester moiety, such as —$CH_2$—C(O)—$OCH_3$, unless the ester is sterically hindered, it is typically metabolized in vivo to yield the carboxylic acid moiety. These metabolites are relatively long-lived, and are believed to be the active form.

In another embodiment, the compounds generally have the following formula:

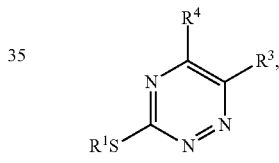

and tautomers, prodrugs, and pharmaceutically-acceptable salts thereof.

In this formula, $R^1$, $R^3$, and $R^4$ are as defined above.

Representative compounds in this embodiment include the following:

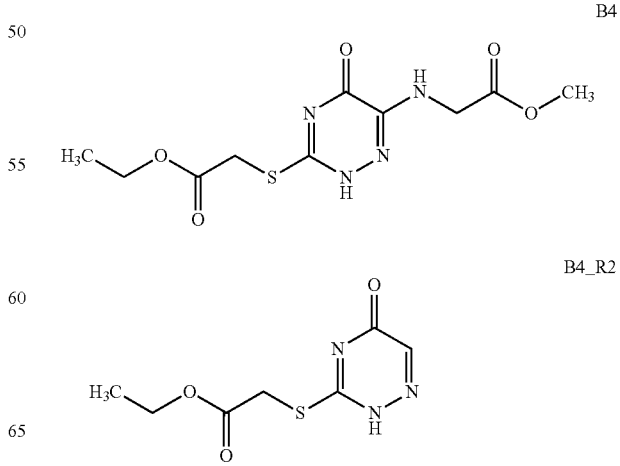

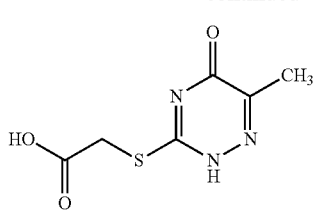

B4_R1

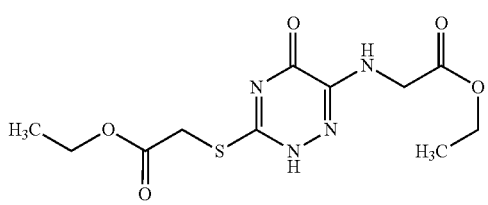

B41

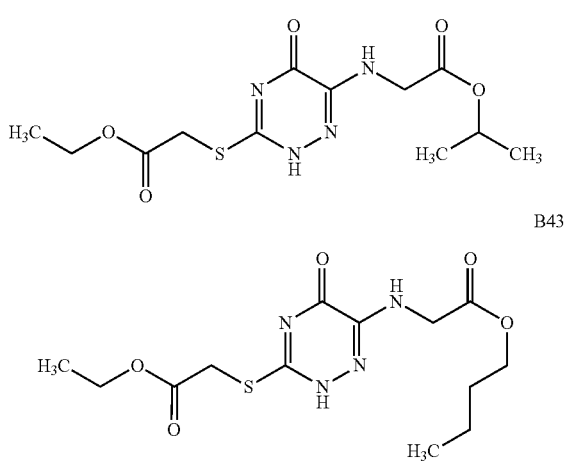

B42

B43

The most active compound in this embodiment is Compound B4 (also known as methyl N-{3-[(2-ethoxy-2-oxo-ethyl)sulfanyl]-5-oxo-2,5-dihydro-1,2,4-triazin-6-yl}glycinate). This compound was found to be extremely active (CASA=11.4 μM).

II. High Throughput Assays

Two different high-throughput assays have been developed. One is a bead-based assay, and the other is an in-silico assay.

AlphaScreen™ Assay

The AlphaScreen assay is a bead-based technology that allows the study of different types of biomolecular interactions. When acceptor and donor beads are brought together (200 nm) by the interacting molecules, the excitation of the donor beads generates singlet-state oxygen molecules (t½; 4 μsec), which initiate a chemiluminescent reaction in the acceptor bead that emits light at 520-620 nm. The AlphaScreen assay was performed in white opaque 384-well microplates (OptiPlate-384; PerkinElmer) in a final volume of 20 or 30 μl depending on the experiment as indicated. Unless otherwise stated, all dilutions were made in assay buffer (100 mM Tris-HCl, 0.1% bovine serum albumin, wt/vol, 0.01% casein, wt/vol, 0.01% Tween-20, vol/vol, pH 8.0). In the AlphaScreen™ IgG (Protein A) detection kit (PerkinElmer), acceptor beads were conjugated with Protein A and donor beads with streptavidin. The experiments were carried out at room temperature and under subdued lighting.

Each recombinant EPPIN construct (wild-type, truncations, and mutants) was preincubated with anti-EPPIN Q20E antibody and Protein A acceptor beads for 30 min. In parallel, recombinant biotinylated (bt)-SEMG1 or bt-LTF was pre-incubated with streptavidin donor beads under the same conditions. Equal volumes of each EPPIN/Q20E/Protein A acceptor beads and bt-SEMG1/streptavidin donor beads or bt-LTF/streptavidin donor beads were pipetted into the plate wells. The final concentration of assay components was 58 nM EPPIN, 1 nM bt-SEMG1 or 4 nM bt-LTF, 2 nM Q20E antibody, and 10 μg/ml beads.

Each set of samples was pipetted in at least four replicates. Plates were covered with top seal and transferred to a Synergy 2 Multiplatform automated plate reader (Biotek). After shaking for 2 min, plates were read every 2 h during 16 h: excitation using a 680/30 filter and emission using a 570/100 filter and data acquired using a modified AlphaScreen™ protocol in the Gen5 software (Biotek). A total of nine time points were generated during each experiment. Negative controls were performed under the same conditions in the absence of EPPIN, bt-SEMG1, or bt-LTF and in the presence of beads only. A specific signal for each time point was calculated by subtracting the background signal (obtained in the absence of bt-SEMG1 or bt-LTF) from its respective total signal. To monitor assay sensitivity and robustness, signal-to-background (SB) ratios and Z0 values were calculated as previously described [Wilson et al., J. Biomol. Screen, 2003; 8:522-532.].

Concentration-Response and Competition Experiments

Concentration-response experiments were carried out as described above using increasing concentrations of wt-EPPIN (1 nM-1 μM) in the presence of constant concentrations of bt-SEMG1 (0.5-4 nM) or bt-LTF (4-8 nM) in a 20 μl-assay volume. Similarly, increasing concentrations of bt-SEMG1 (0.1 μM-1 nM) or bt-LTF (3 pM-8 nM) were incubated in the presence of a constant concentration of EPPIN (58 nM). The bead concentration was 10 μg/ml. Specific counts for each data point were calculated as described above and used for the determination of $EC_{50}$ values by nonlinear regression curve fitting. For competition experiments, wt-EPPIN (10 or 30 nM) and bt-SEMG1 (1 nM) or bt-LTF (2 nM) were incubated in the presence of increasing concentrations of nonbiotinylated SEMG1 (10 pM-150 nM) or LTF (100 pM-600 nM) in a 30 μl-assay volume. In this case, wt-EPPIN and bt-SEMG1 or bt-LTF were pre-incubated with their respective beads as described above, and the solutions were pipetted into the plate wells in the following order: 5 μl competitor protein dilutions, 10 μl of wt-EPPIN/Q20E/Protein A acceptor beads, and 15 μl of bt-SEMG1/streptavidin donor beads or bt-LTF/streptavidin donor beads. The bead concentration was 15 μg/ml. A specific signal for each competitor concentration point was calculated as described above. The $IC_{50}$ values were calculated by nonlinear regression curve fitting using the normalized data as a percentage of the specific binding in the absence of competitor. AlphaScreen TruHits assay was used as a positive control (for nonspecific effects) under the same conditions as described in the Supplemental Methods.

EPPIN Homology Modeling

Three-dimensional homology models for the EPPIN C-terminal region (K73-P133) were built using the SWISS-MODEL Workspace [Arnold et al., Bioinformatics 2006; 22:195-201; Schwede et al., Nucleic Acids Res 2003; 31:3381-3385; and Bordoli et al., Nat Protocols 2008; 4:1-13.]. After template identification, four templates were chosen (Protein Data Bank identification [PDB ID]) based on the percentage of sequence identity to EPPIN C-terminus: bovine trypsin inhibitor (aprotinin; 1bpiA), boophilin (2odyE), textilinin-1 (3bybB), and alpha3 chain of human type VI collagen (1kthA). EPPIN structural models were then generated using the described templates as reference structures. The quality of the resulting three-dimensional models was compared using QMEAN Z-score (global quality of the generated model) [22]. We selected the model with the highest QMEAN Zscore and then created EPPIN C-terminal model figures using Swiss-PDB Viewer 4.04 (Swiss Institute of Bioinformatics) and rendered with POV-Ray 3.6 (Persistence of Vision Raytracer Pty Ltd).

In one embodiment, a computer program is used to manage the assay, by recording the identity of the compounds, and one or more properties of the compounds, such as their binding affinity to the relevant site, their activity, and the like. In this manner, a series of high-throughput multi-well plates can be screened, and the identity of compounds that inhibit EPPIN-semenogelin binding stored for later use. Such computer programs are well known to those of skill in the art of high throughput screening.

II. Compound Synthesis

The compounds of the first embodiment can be prepared using the following general reactions:

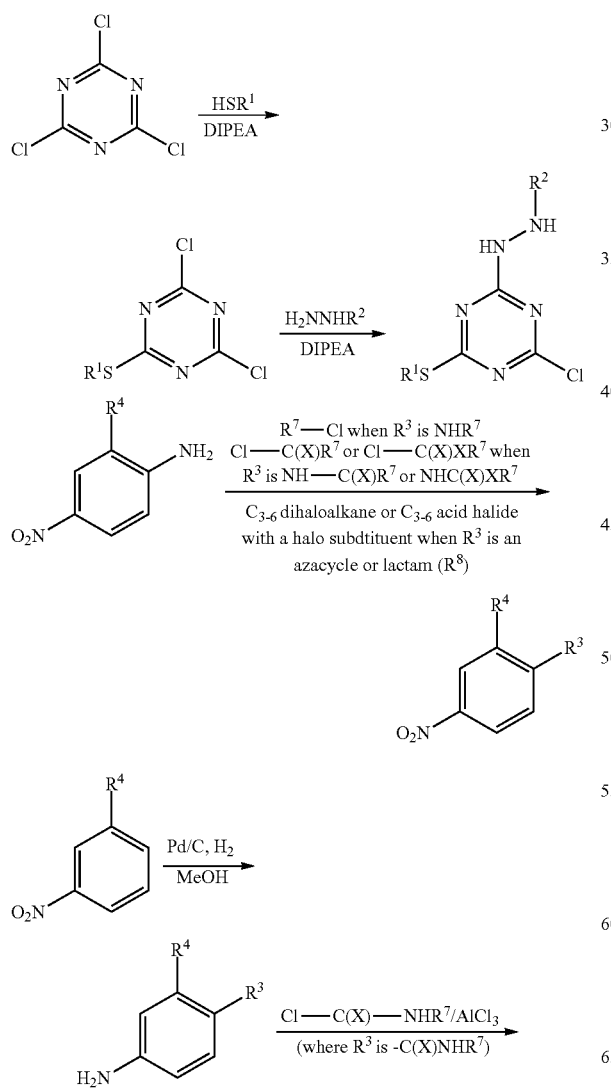

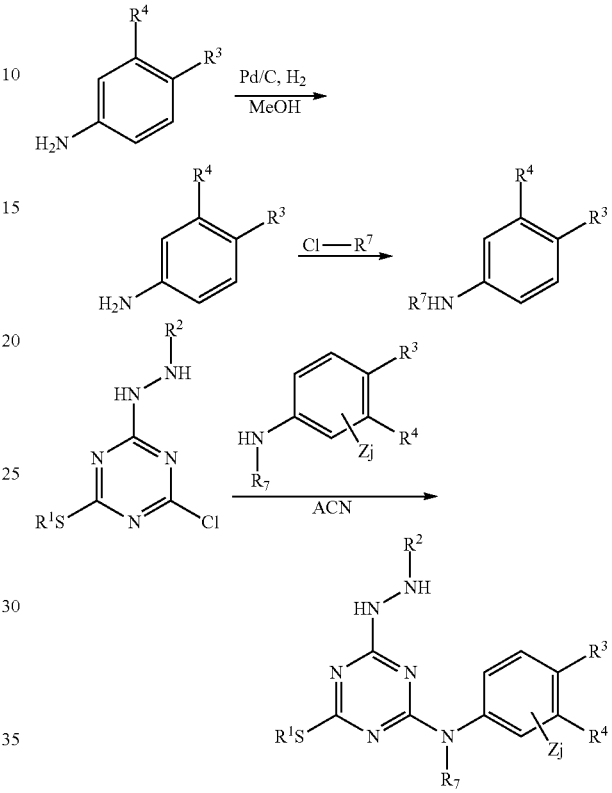

where DIPEA is N,N-Diisopropylethylamine, ACN is acrylonitrile, MeOH is methanol, $H_2$ is hydrogen, and Pd is palladium.

Where the heteraryl is not triazine, the following starting material can be used:

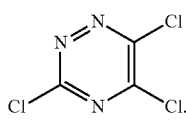

In some embodiments, $-SR^1$ is $-SCH_2C(O)OR_7$, an ester which is metabolized to form a carbocyclic acid. These metabolites are active compounds, and can be administered as active compounds. When synthesizing these compounds, to the extent that the carboxylic acid moiety would interfere with any of the reactions used to prepare the final compounds, the carboxylic acid moiety can be protected with a suitable protecting group, and deprotected at a later stage in the synthesis. Benzyl esters are one example of a suitable protecting group, and these esters can be reacted with hydrogen to form the free acid and toluene.

The compounds described herein all include at least one aryl ring, and each ring can, independently, be further substituted with one or more substituents, as defined herein. Those skilled in the art will readily understand that incorporation of other substituents onto an aryl ring used as a starting material to prepare the compounds described herein, and other positions in the compound framework, can be readily realized. Such substituents can provide useful properties in and of themselves or serve as a handle for further synthetic elaboration.

Benzene rings can be substituted using known chemistry, including the reactions discussed below. For example, alkyl substituents can be added using Friedel craft alkylation reactions. Biphenyl compounds can be synthesized by treating aryl phenylmagnesium bromides with copper salts, by the oxidative dehydrogenation of the aryl rings, or the dealkylation of toluene or other methyl-substituted aromatic rings.

Aryl rings can be nitrated, and the resulting nitro group on the aryl ring reacted with sodium nitrite to form a diazonium salt. The diazonium salt can be manipulated using known chemistry to form various substituents on a benzene ring.

Diazonium salts can be halogenated using various known procedures, which vary depending on the particular halogen. Examples of suitable reagents include bromine/water in concentrated HBr, thionyl chloride, pyr-ICl, fluorine and Amberlyst-A.

A number of other analogs, bearing substituents in the diazotized position, can be synthesized from the corresponding amino compounds, via the diazo intermediate. The diazo compounds can be prepared using known chemistry, for example, as described above.

Nitro derivatives can be reduced to the amine compound by reaction with a nitrite salt, typically in the presence of an acid. Other substituted analogs can be produced from diazonium salt intermediates, including, but are not limited to, hydroxy, alkoxy, fluoro, chloro, iodo, cyano, and mercapto, using general techniques known to those of skill in the art.

For example, hydroxy-aromatic analogues can be prepared by reacting the diazonium salt intermediate with water. Halogens on an aryl ring can be converted to Grignard or organolithium reagents, which in turn can be reacted with a suitable aldehyde or ketone to form alcohol-containing side chains. Likewise, alkoxy analogues can be made by reacting the diazo compounds with alcohols. The diazo compounds can also be used to synthesize cyano or halo compounds, as will be known to those skilled in the art. Mercapto substitutions can be obtained using techniques described in Hoffman et al., J. Med. Chem. 36: 953 (1993). The mercaptan so generated can, in turn, be converted to an alkylthio substituent by reaction with sodium hydride and an appropriate alkyl bromide. Subsequent oxidation would then provide a sulfone. Acylamido analogs of the aforementioned compounds can be prepared by reacting the corresponding amino compounds with an appropriate acid anhydride or acid chloride using techniques known to those skilled in the art of organic synthesis.

Hydroxy-substituted analogs can be used to prepare corresponding alkanoyloxy-substituted compounds by reaction with the appropriate acid, acid chloride, or acid anhydride. Likewise, the hydroxy compounds are precursors of both the aryloxy via nucleophilic aromatic substitution at electron deficient aromatic rings. Such chemistry is well known to those skilled in the art of organic synthesis. Ether derivatives can also be prepared from the hydroxy compounds by alkylation with alkyl halides and a suitable base or via Mitsunobu chemistry, in which a trialkyl- or triarylphosphine and diethyl azodicarboxylate are typically used. See Hughes, Org. React. (N.Y.) 42: 335 (1992) and Hughes, Org. Prep. Proced. Int. 28: 127 (1996) for typical Mitsunobu conditions.

Cyano-substituted analogs can be hydrolyzed to afford the corresponding carboxamido-substituted compounds. Further hydrolysis results in formation of the corresponding carboxylic acid-substituted analogs. Reduction of the cyano-substituted analogs with lithium aluminum hydride yields the corresponding aminomethyl analogs. Acyl-substituted analogs can be prepared from corresponding carboxylic acid-substituted analogs by reaction with an appropriate alkyllithium using techniques known to those skilled in the art of organic synthesis.

Carboxylic acid-substituted analogs can be converted to the corresponding esters by reaction with an appropriate alcohol and acid catalyst. Compounds with an ester group can be reduced with sodium borohydride or lithium aluminum hydride to produce the corresponding hydroxymethyl-substituted analogs. These analogs in turn can be converted to compounds bearing an ether moiety by reaction with sodium hydride and an appropriate alkyl halide, using conventional techniques. Alternatively, the hydroxymethyl-substituted analogs can be reacted with tosyl chloride to provide the corresponding tosyloxymethyl analogs, which can be converted to the corresponding alkylaminoacyl analogs by sequential treatment with thionyl chloride and an appropriate alkylamine. Certain of these amides are known to readily undergo nucleophilic acyl substitution to produce ketones.

Hydroxy-substituted analogs can be used to prepare N-alkyl- or N-arylcarbamoyloxy-substituted compounds by reaction with N-alkyl- or N-arylisocyanates. Amino-substituted analogs can be used to prepare alkoxycarboxamido-substituted compounds and urea derivatives by reaction with alkyl chloroformate esters and N-alkyl- or N-arylisocyanates, respectively, using techniques known to those skilled in the art of organic synthesis.

Any of the aforementioned substituents can be present on any or all of the aromatic rings in the compounds described herein.

The compounds in the second embodiment can be prepared using the following general reaction schemes. It is to be understood that these process steps will produce various isomeric forms, so product separation will likely be required between steps. Amine and hydroxyl groups can be further elaborated using known chemistry, for example, amidation, esterification, etherification, and the like.

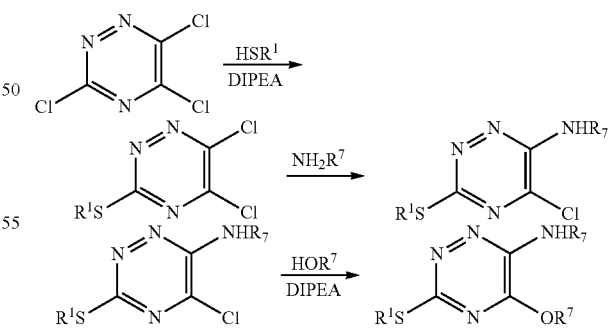

III. Pharmaceutical Compositions Including the Compounds

Temporary and reversible male contraception can be achieved by administering to the patient an effective amount of the compounds described above, in the presence of a pharmaceutically acceptable carrier or diluent, using any of the modes of administration as described in detail herein. Of course, the treatment is not necessarily reversible on any one ejaculate, but once one stops taking/using the compound, the effect on sperm motility will cease and the infertility will be reversed.

The active materials can be administered by any appropriate route, for example, orally, parenterally, enterally, intravenously, intradermally, subcutaneously, transdermally, intranasally or topically, in liquid or solid form. Ideally, the compounds are delivered orally or transdermally, to ensure maximal patient compliance.

The active compounds are included in the pharmaceutically acceptable carrier or diluent in an amount sufficient to deliver to a patient a therapeutically effective amount of compound to inhibit sperm motility without causing serious toxic effects in the treated patient. By "inhibitory amount" is meant an amount of active ingredient sufficient to exert an inhibitory effect on sperm motility as measured by, for example, an assay such as the ones described herein.

A preferred dose of the compound for all the abovementioned conditions will be in the range from about 1 to 75 mg/kg, preferably 1 to 20 mg/kg, of body weight per day, more generally 0.1 to about 100 mg per kilogram body weight of the recipient per day. The effective dosage range of the compounds can be calculated by means known to those skilled in the art.

The compounds are conveniently administered in unit any suitable dosage form, including but not limited to one containing 7 to 3000 mg, preferably 70 to 1400 mg of active ingredient per unit dosage form. An oral dosage of 50 to 1000 mg is usually convenient.

The concentration of active compound in the drug composition will depend on absorption, distribution, metabolism and excretion rates of the drug as well as other factors known to those of skill in the art. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible bind agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. Syrups may contain, in addition to the active compounds, sucrose as a sweetening agent and certain preservatives, dyes and colorings and flavors.

Solutions or suspensions used for parental, intradermal, subcutaneous, or topical application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Controlled Release Formulations

All of the U.S. patents cited in this section on controlled release formulations are incorporated by reference in their entirety.

The field of biodegradable polymers has developed rapidly since the synthesis and biodegradability of polylactic acid was reported by Kulkarni et al., in 1966 ("Polylactic acid for surgical implants," Arch. Surg., 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers). See also U.S. Pat. No. 5,626,863 to Hubbell, et al which describes photopolymerizable biodegradable hydrogels as tissue contacting materials and controlled release carriers (hydrogels of polymerized and crosslinked macromers comprising hydrophilic oligomers having biodegradable monomeric or oligomeric extensions, which are end capped monomers or oligomers capable of polymerization and crosslinking); and PCT WO 97/05185 filed by Focal, Inc. directed to multiblock biodegradable hydrogels for use as controlled release agents for drug delivery and tissue treatment agents.

Degradable materials of biological origin are well known, for example, crosslinked gelatin. Hyaluronic acid has been crosslinked and used as a degradable swelling polymer for biomedical applications (U.S. Pat. No. 4,957,744 to Della Valle et. al.; (1991) "Surface modification of polymeric biomaterials for reduced thrombogenicity," Polym. Mater. Sci. Eng., 62:731 735]).

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

U.S. Pat. No. 5,641,745 to Elan Corporation, PLC discloses a controlled release pharmaceutical formulation which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 to Elan Corporation plc describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. No. 5,505,962 describes a controlled release pharmaceutical formulation.

Transdermal Delivery

The compositions for transdermal administration include the active compounds, or their pharmaceutically acceptable salts, including fatty acid salts, and optionally can also include other ingredients including, but not limited to, carriers and excipients, such as permeation enhancers which promote transdermal absorption of the active ingredient after transdermal administration.

Relative to an oral dosage form such as a tablet or capsule, transdermal delivery can provide both more rapid or more sustained absorption, controlled release and therefore controlled onset of therapeutic action, and avoidance of liver first pass metabolism. For patients who have difficulty in swallowing tablets, capsules or other solids or those who have intestinal failure, the transdermal delivery route can be preferred. This route of administration can also be preferred for its ease of use, and for patients who otherwise might forget to take once-daily pills.

The amount of drug absorbed depends on many factors. These factors include the drug concentration, the drug delivery vehicle, skin contact time, the area of the skin dosed, the ratio of the ionized and unionized forms of the drug at the pH of the absorption site, the molecular size of the drug molecule, the drug's relative lipid solubility, and the relative affinity of the drug for the skin versus the formulation (if drug is not readily released from its formulation matrix, very little drug absorption will be realized). Those of skill in the art can readily prepare an appropriate transdermal composition, which delivers an appropriate amount of the active agent, taking these factors into consideration.

Transdermal Devices

The transdermal device for delivering the compounds described herein can be of any type known in the art, including the monolithic, matrix, membrane, and other types typically useful for administering drugs by the transdermal route. Such devices are disclosed in U.S. Pat. Nos. 3,996,934; 3,797,494; 3,742,951; 3,598,122; 3,598,123; 3,731,683; 3,734,097; 4,336,243; 4,379,454; 4,460,372; 4,486,193; 4,666,441; 4,615,699; 4,681,584; and U.S. Pat. Nos. 4,558,580, 5,533,995, among others; the disclosures of which are incorporated herein by reference.

These devices tend to be flexible, adhere well to the skin, and have a polymeric backing (covering) that is impermeable to the drug to be delivered, so that the drug is administered through the skin. The drug, or pharmaceutically acceptable salt thereof, is typically present in a solution or dispersion, which can be in the form of a gel, and which aids in drug delivery through the stratum corneum of the epidermis and to the dermis for absorption.

Membrane Devices

Membrane devices typically have four layers: (1) an impermeable backing, (2) a reservoir layer, (3) a membrane layer (which can be a dense polymer membrane or a microporous membrane), and (4) a contact adhesive layer which either covers the entire device surface in a continuous or discontinuous coating or surrounds the membrane layer. Examples of materials that may be used to act as an impermeable layer are high, medium, and low density polyethylene, polypropylene, polyvinylchloride, polyvinylidene chloride, polycarbonate, polyethylene terephthalate, and polymers laminated or coated with aluminum foil. Others are disclosed in the standard transdermal device patents mentioned herein. In certain embodiments in which the reservoir layer is fluid or is a polymer, the outer edge of the backing layer can overlay the edge of the reservoir layer and be sealed by adhesion or fusion to the diffusion membrane layer. In such instances, the reservoir layer need not have exposed surfaces.

The reservoir layer is underneath the impermeable backing and contains a carrier liquid, typically water and/or an alcohol, or polyol or ester thereof, and may or may not contain the active compounds. The amount of drug in the reservoir depends on the desired rate of absorption through the skin from the device and the intended duration of therapy. The reservoir layer can include diluents, stabilizers, vehicles, gelling agents, and the like in addition to the carrier liquid and active compounds.

The diffusion membrane layer of the laminate device can be made of a dense or microporous polymer film that has the requisite permeability to the drug and the carrier liquid. Preferably, the membrane is impermeable to ingredients other than the drug and the carrier liquid, although when buffering at the skin surface is desired, the membrane should be permeable to the buffer in the formulation as well. Examples of polymer film that may be used to make the membrane layer are disclosed in U.S. Pat. Nos. 3,797,454 and 4,031,894. The preferred materials are polyurethane, ethylene/vinyl alcohol copolymers or ethylene/vinyl acetate.

Monolithic Matrices

The second class of transdermal systems is represented by monolithic matrices. Examples of such monolithic devices are U.S. Pat. Nos. 4,291,014, 4,297,995, 4,390,520, and 4,340,043. Others are known to those of ordinary skill in this art.

Monolithic and matrix type barrier transdermal devices typically include:

(1) Porous polymers or open-cell foam polymers, such as polyvinyl chloride (PVC), polyurethanes, polypropylenes, etc.

(2) Highly swollen or plasticized polymers such as cellulose, HEMA or MEMA or their copolymers, hydroxypropyl methylcellulose (HPMC), hydroxyethyl methylcellulose (HEMC), and the like, polyvinyl alcohol (PVA)/polyvinylpyrollidone (PVP), or other hydrogels, or PVC, polyurethane, ethylene/vinyl acetate, or their copolymers.

(3) Gels of liquids, typically including water and/or hydroxyl-containing solvents such as ethanol, and often containing gelling agents such PVP, carboxymethylcellulose (CMC), Klucel, HPMC, alginates, kaolinate, bentonite, or montmorillonite, other clay fillers, stearates, silicon dioxide particles, etc.

(4) Nonwoven materials made of textiles, celluloses, polyurethanes, polyester or other fiber.

(5) Sponges, which can be formed from natural or foamed polymers.

(6) Adhesives, ideally dermatologically-acceptable pressure sensitive adhesives, for example, silicone adhesives or acrylic adhesives.

The various components for the transdermal formulations are described in more detail below.

Polymeric Barrier Materials

Representative polymeric barrier materials include, but are not limited to:

Polycarbonates, such as those formed by phosgenation of a dihydroxy aromatic such as bisphenol A, including materials are sold under the trade designation Lexan® (the General Electric Company);

Polyvinylchlorides, such as Geon® 121 (B. G. Goodrich Chemical Company);

Polyamides ("nylons"), such as polyhexamethylene adipamide, including NOMEX® (E. I. DuPont de Nemours & Co.).

Modacrylic copolymers, such as DYNEL®, are formed of polyvinylchloride (60 percent) and acrylonitrile (40 percent), styrene-acrylic acid copolymers, and the like.

Polysulfones, for example, those containing diphenylene sulfone groups, for example, P-1700 (Union Carbide Corporation).

Halogenated polymers, for example, polyvinylidene fluoride, such as Kynar® (Pennsalt Chemical Corporation), polyvinylfluoride, such as Tedlar® (E. I. DuPont de Nemours & Co.), and polyfluorohalocarbons, such as Aclar® (Allied Chemical Corporation).

Polychlorethers, for example, Penton® (Hercules Incorporated), and other thermoplastic polyethers.

Acetal polymers, for example, polyformaldehydes, such as Delrin® (E. I. DuPont de Nemours & Co.).

Acrylic resins, for example, polyacrylonitrile, polymethyl methacrylate (PMMA), poly n-butyl methacrylate, and the like.

Other polymers such as polyurethanes, polyimides, polybenzimidazoles, polyvinyl acetate, aromatic and aliphatic, polyethers, cellulose esters, e.g., cellulose triacetate; cellulose; colledion (cellulose nitrate with 11% nitrogen); epoxy resins; olefins, e.g., polyethylene, polypropylene; polyvinylidene chloride; porous rubber; cross linked poly(ethylene oxide); cross-linked polyvinylpyrrolidone; cross-linked poly (vinyl alcohol); polyelectrolyte structures formed of two ionically associated polymers of the type as set forth in U.S. Pat. Nos. 3,549,016 and 3,546,141; derivatives of polystyrene such as poly(sodium styrenesulfonate) and poly(vinylbenzyltrimethyl-ammonium chloride); poly(hydroxyethylmethacrylate); poly(isobutylvinyl ether), and the like, may also be used. A large number of copolymers which can be formed by reacting various proportions of monomers from the above list of polymers are also useful.

If the membrane or other barrier does not have a sufficiently high flux, the thickness of the membrane or barrier can be reduced. However, the thickness should not be reduced to the point where it is likely to tear, or to a point where the amount of drug which can be administered is too low.

Adhesives

The transdermal drug delivery formulations typically include a contact adhesive layer to adhere the device to the skin. The active agent may, in some embodiments, reside in the adhesive.

Exemplary adhesives include polyurethanes; acrylic or methacrylic resins such as polymers of esters of acrylic or methacrylic acid with alcohols such as n-butanol, n-pentanol, isopentanol, 2-methylbutanol, 1-methylbutanol, 1-methylpentanol, 2-methylpentanol, 3-methylpentanol, 2-ethylbutanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tertbutylacrylamide, itaconic acid, vinylacetate, N-branched alkyl maleamic acids wherein the alkyl group has 10 to 24 carbon atoms, glycol diacrylates, or mixtures of these; natural or synthetic rubbers such as styrenebutadiene, butylether, neoprene, polyisobutylene, polybutadiene, and polyisoprene; polyvinylacetate; ureaformaldehyde resins; phenolformaldehyde resins; resorcinol formaldehyde resins, cellulose derivatives such as ethylcellulose, methylcellulose, nitrocellulose, cellulose acetatebutyrate, and carboxymethyl cellulose; and natural gums such as guar, acacia, pectins, starch, dextrin, albumin, gelatin, casein, etc. The adhesives can be compounded with tackifiers and stabilizers, as is well known in the art.

Representative silicone adhesives include silicone elastomers based on monomers of silanes, halosilanes, or $C_{1-18}$ alkoxysilanes, especially polydimethylsiloxanes which may be used alone or formulated with a silicone tackifier or silicone plasticizer which are selected from medically acceptable silicone fluids, i.e. non-elastomeric silicones based on silanes, halosilanes or $C_{1-18}$ alkoxysilanes. Typical silicone adhesives are available from Dow Corning under the tradename SILASTIC®.

Liquid Vehicles

Transdermal formulations can include a variety of components, including a liquid vehicle, typically a $C_{2-4}$ alkanol such as ethanol, isopropanol, n-propanol, butanol, a polyalcohol or glycol such as propylene glycol, butylene glycol, hexylene glycol, ethylene glycol, and/or purified water. The vehicle is typically present in an amount of between about 5 and about 75% w/w, more typically, between about 15.0% and about 65.0% w/w, and, preferably, between about 20.0 and 55.0% w/w. Water augments the solubility of hydrophilic active agents in the formulation, and accelerates the release of lipophilic active agents from a formulation. Alcohols, such as ethanol, increase the stratum corneum liquid fluidity or function to extract lipids from the stratum corneum. As discussed herein, the glycols can also act as permeation enhancers.

Permeation Enhancers

Successful transdermal delivery depends on sufficient flux of the drug across skin, and sufficient surface area of skin, to produce an efficacious plasma concentration of the drug. For reasons of consumer acceptance, the practical surface area of a transdermal system is limited from approximately 5 to 100 cm². With this limitation on surface area, the therapeutic transdermal administration of many drugs requires an increase in the inherent skin permeability to obtain the necessary flux. Accordingly, compounds have been developed which enhance percutaneous absorption of the drugs to be administered.

Permeation enhancers are described, for example, in U.S. Pat. Nos. 5,785,991; 4,764,381; 4,956,171; 4,863,970; 5,453,279; 4,883,660; 5,719,197, and in the literature "Pharmaceutical Skin Penetration Enhancement", J. Hadgraft, Marcel Dekker, Inc. 1993; "Percutaneous Absorption", R. Bronaugh, H. Maibach, Marcel Dekker, Inc. (1989), B. W. Barry, "Penetration Enhancers in Skin Permeation", Proceedings of the 13th international Symposium on Controlled Release of Bioactive Materials, ed. by Chaudry & Thies, Controlled Release Society, Lincolnshire, Ill., pp. 136-137 (1986), and Cooper & Berner, "Penetration Enhancers", in The Transdermal Delivery of Drugs, Vol. II ed. by Kydonieus and Berner, CRC Press, Boca Raton, Fla. pp. 57-62 (1986), the contents of each of which are hereby incorporated by reference.

The permeation enhancers should both enhance the permeability of the skin, and be non-toxic, non-irritant and non-sensitizing on repeated exposure. Representative permeation enhancers include, for example, sucrose monococoate, glycerol monooleate, sucrose monolaurate, glycerol monolaureate, diethylene glycol monoalkyl ethers such as diethylene glycol monoethyl or monomethyl ether (Transcutol® P), ester components such as propylene glycol monolaurate, methyl laurate, and lauryl acetate, monoglycerides such as glycerol monolaurate, fatty alcohols such as lauryl alcohol, and 2-ethyl-1,3 hexanediol alone or in combination with oleic acid.

In one embodiment, the transdermal compositions are provided with skin permeation enhancing benefits by combining the active compounds with saturated fatty alcohols, or forming salts of the compounds with one or more fatty acids, such as those of the formula $CH_3—(CH_2)_n—CH_2OH$ or $CH_3—(CH_2)_n—CH_2COOH$ respectively, in which n is an integer from 8 to 22, preferably 8 to 12, most preferably 10 or an unsaturated fatty alcohol or fatty acid given by the formula $CH_3—(C_nH_2(n-x))—OH$ or $CH_3—(C_nH_2(n-x))—COOH$ respectively in which n is an integer from 8 to 22 and x is the number of double bonds; and preferably also a second component that is a monoalkyl ether of diethylene glycol, preferably diethylene glycol monoethyl ether or diethylene glycol monomethyl ether, in a vehicle or carrier composition, integrated by an $C_{1-4}$ alcohol, preferably ethanol; a polyalcohol, preferably propylene glycol and purified water.

A binary system including a combination of oleic acid or oleic alcohol and a lower alcohol, or a combination of a lower alkyl ester of a polycarboxylic acid, an aliphatic monohydroxy alcohol and an aliphatic diol, can be used.

Representative permeation enhancers include fatty alcohols and fatty acids, and monoalkyl ethers of diethylene glycol such as diethylene glycol monoethyl ether or diethylene glycol monomethyl ether. The fatty alcohols are typically present in an amount of between about 0.1 and about 20.0% w/w, preferably between about 0.2 and about 10.0% w/w, and more preferably, between about 0.4 and about 3.0% w/w. The diethylene glycol monoalkyl ethers are typically present in an amount up to 40.0% w/w, preferably between about 0.2 and 25.0% w/w, and, more preferably, between about 2.0 and about 8.0% w/w.

Although not wishing to be bound to a particular theory, it is believed that the mechanism by which certain permeation enhancers function to enhance permeability of the active agents through the stratum corneum is as follows:

The fatty alcohol is mainly distributed to the stratum corneum because of its lipophilicity and interacts with the stratum corneum lipids.

The diethylene glycol monoalkyl ethers dissolve both hydrophilic and a lipophilic active agents therein, and facilitates the penetration of the active agents to the skin.

Glycols, such as propylene glycol, act as a cosolvent of the active agents, and thus increase their solubility in the formulation. Further, they tend to solvate the intracellular keratin of the stratum corneum, and thus enhance drug mobility and skin hydration.

Gelling Agents

Gelling agents, such as carbomer, carboxyethylene or polyacrylic acid such as Carbopol® 980 or 940 NF, 981 or 941 NF, 1382 or 1342 NF, 5984 or 934 NF, ETD 2020, 2050, 934P NF, 971P NF, 974P NF, Noveon® AA-1 USP, etc; cellulose derivatives such as ethylcellulose, hydroxypropylmethylcellulose (HPMC), ethylhydroxyethylcellulose (EHEC), carboxymethylcellulose (CMC), hydroxypropylcellulose (HPC) (Klucel®, different grades), hydroxyethylcellulose (HEC) (Natrosol® grades), HPMCP 55, Methocel® grades, etc; natural gums such as arabic, xanthan, guar gums, alginates, etc; polyvinylpyrrolidone derivatives such as Kollidon® grades; polyoxyethylene polyoxypropylene copolymers such as Lutrol® F grades 68, 127, etc; others like chitosan, polyvinyl alcohols, pectins, veegun grades, et, can also be present. Those of the skill in the art know of other gelling agents or viscosants suitable for use in the present invention.

Representative gelling agents include, but are not limited to, Carbopol® 980 NF, Lutrol® F 127, Lutrol® F 68 and Noveon® AA-1 USP. The gelling agent is present from about 0.2 to about 30.0% w/w, depending on the type of polymer.

Preservatives

The transdermal compositions can also include one or more preservatives and/or antioxidants. Representative preservatives include quaternary ammonium salts such as lauralkonium chloride, benzalkonium chloride, benzododecinium chloride, cetyl pyridium chloride, cetrimide, domiphen bromide; alcohols such as benzyl alcohol, chlorobutanol, o-cresol, phenylethyl alcohol; organic acids or salts thereof such as benzoic acid, sodium benzoate, potassium sorbate, parabens; or complex forming agents such as EDTA. Representative antioxidants include butylhydroxytoluene, butylhydroxyanisole, ethylenediaminetetraacetic acid and its sodium salts, D,L-alpha tocoferol.

Other Components

Other components may include diluents such as cellulose, microcrystalline cellulose, hydroxypropyl cellulose, starch, hydroxypropylmethyl cellulose and the like. Excipients can be added to adjust the tonicity of the composition, such as sodium chloride, glucose, dextrose, mannitol, sorbitol, lactose and the like. Acidic or basic buffers can also be added to control the pH. Co-solvents or solubilizers such as glycerol, polyethylene glycols, polyethylene glycols derivatives, polyethylene glycol 660 hydroxystearate (Solutol HS 15 from BASF), butylene glycol, hexylene glycol, and the like, can also be added.

Controlled Release of the Active Agent

The administration of the active agent can be controlled by using controlled release formulations, which can provide rapid or sustained release, or both, depending on the formulations.

There are numerous particulate drug delivery vehicles known to those of skill in the art which can include the active ingredients, and deliver them in a controlled manner. Examples include particulate polymeric drug delivery vehicles, for example, biodegradable polymers, and particles formed of non-polymeric components. These particulate drug delivery vehicles can be in the form of powders, microparticles, nanoparticles, microcapsules, liposomes, and the like. Typically, if the active agent is in particulate form without added components, its release rate depends on the release of the active agent itself. In contrast, if the active agent is in particulate form as a blend of the active agent and a polymer, the release of the active agent is controlled, at least in part, by the removal of the polymer, typically by dissolution or biodegradation.

In some embodiments, the compositions can provide an initial rapid release of the active ingredient followed by a sustained release of the active ingredient. U.S. Pat. No. 5,629,011 provides examples of this type of formulation and is incorporated herein by reference in its entirety. There are numerous transdermal compositions that use transdermal delivery to deliver nicotine in a time-release manner (such as rate-controlling membranes), including currently marketed therapies for female contraception and nicotine replacement. These are also suitable for administering the compounds described herein.

IV. Methods of Providing Reversible and Temporary Male Contraception

The compounds and compositions for oral or transdermal administration can be used to provide reversible and temporary male contraception. Because the compounds function by mimicking the binding of anti-EPPIN antibodies to EPPIN, or inhibiting or enhancing the binding of EPPIN and semenogelin, once administration of the compounds is terminated, the inhibition of this binding will be terminated, thus restoring fertility.

In one aspect, the compounds are administered orally, preferably in a once-daily format, to provide male contraception. In another aspect, the compounds are administered transdermally, ideally in a lesser frequency, such as once weekly or once monthly, to provide male contraception.

Those of skill in the art can effectively follow the administration of these therapies without undue experimentation. Until an appropriate dosage is determined for an individual patient, it may be desirable to have the patient take the dosage for a particular amount of time, for example, a week or a month, with periodic measurement of sperm motility, to ensure that the dosage for the particular patient is the right dosage. As with female contraception, the compositions may be provided in several different dosage levels, to provide an optimal dosage for each patient. The optimal dosage is, ideally, one which reliably provides contraception, but does not significantly exceed the dosage required to achieve such contraception.

V. Spermicidal Compositions

For certain individuals, it can be equally important to prevent transmission of disease as it is to prevent pregnancy. Thus, it can be desirable to use the compounds described herein to inhibit spermatozoa forward motility (thus inhibiting fertilization) in conjunction with a condom.

For certain other individuals, there is a desire to prevent pregnancy, a desire (in the individual or in their partner) to avoid taking an oral contraceptive agents, and a desire to avoid using condoms. For these individuals, it can be desirable to use the compounds described herein to inhibit spermatozoa forward motility (thus inhibiting fertilization) in conjunction with a diaphragm, female condom, or spermicidal lubricant or jelly.

In these embodiments, the compositions may include other agents, such as those that locally inhibit viral, fungal, and/or bacterial infections.

Lubricant Compositions

In one embodiment, the compounds described herein are present in prophylactic lubricant compositions for use during sexual relations. The lubricant compositions can be used without condoms, female condoms, or diaphragms, but when used in conjunction with such devices, can provide an additional safety margin, in case the conventional devices are defective.

The lubricant compositions typically include an effective lubricant, an effective concentration of the active compound, and, optionally, an antimicrobial compound effective in destroying the human immunodeficiency virus (HIV, such as HIV-1 and HIV-2), herpes virus, human pappiloma virus (HPV), hepatitis B or C (HBV and HCV) and other viruses and/or bacteria, such as syphilis, gonorrhea, or *Chlamydia*, or fungi, such as those which cause yeast infections. The antimicrobial compound can also be a spermicide which acts in a manner differently than the instant compounds (i.e., does not inhibit EPPIN-semenogelin binding or inhibit spermatozoa forward motility). For example, certain compounds react with the vaginal mucosa to form a barrier to the penetration of sperm cells into the uterus, without substantial detrimental side effects.

The prophylactic lubricant compositions can also include a fungicide, such as methylparaben.

One representative antimicrobial compound is chlorhexidine and its salts, particularly the gluconate or digluconate salts. Chlorhexidine diffuses into the cervical mucous, creating a suspension that restricts penetration of sperm cells during ovulation and also causes them to rapidly lose their mobility. This occurs at concentrations of chlorhexidine in excess of 0.1%. Thus, by using chlorhexidine as the active antimicrobial compound in accordance with the present invention, the chlorhexidine diffuses into the cervical mucous prior to the ejection of semen and in effect creates the "sealed bag" of the vagina, which will retain all the body secretions including the semen. Any viruses present can also be destroyed by the chlorhexidine, which, in concentrations above 0.1%, effectively destroys the envelope of the virus and in so doing prevents the virus from penetrating the human cell.

Thus, lubricant that includes the compounds described herein and an antimicrobial compound can be applied to the sex organs to reduce the friction between the penis and the vaginal wall, kill any bacteria and viruses in the body fluids, and inhibit sperm motility (and possibly also destroy sperm).

Ideally, the pH of the lubricant compositions approximates that of the vaginal tissues, since these tissues could otherwise be inhibited from regenerating if the pH of the lubricant is significantly outside of this normal range.

The lubricant may be any effective lubricant or combination of lubricants acceptable for cosmetic applications. The lubricant compositions can include an alcohol or mixtures of alcohols, and are preferably water-soluble so they can be used with condoms, female condoms and diaphragms, and also to minimize any stains that might form on clothing or sheets. Any water-soluble lubricants can be used, though preferred lubricants include glycerol and propylene glycol. Representative water-soluble lubricants include those in KY-jelly and other water-based lubricant compositions.

The present invention will be better understood with reference to the following non-limiting examples.

Example 1

Synthetic Approaches to Making the Compounds Described Herein

The structures for compounds TZ4_121, TZ4_125 and TZ4_132, as described herein, are shown below.

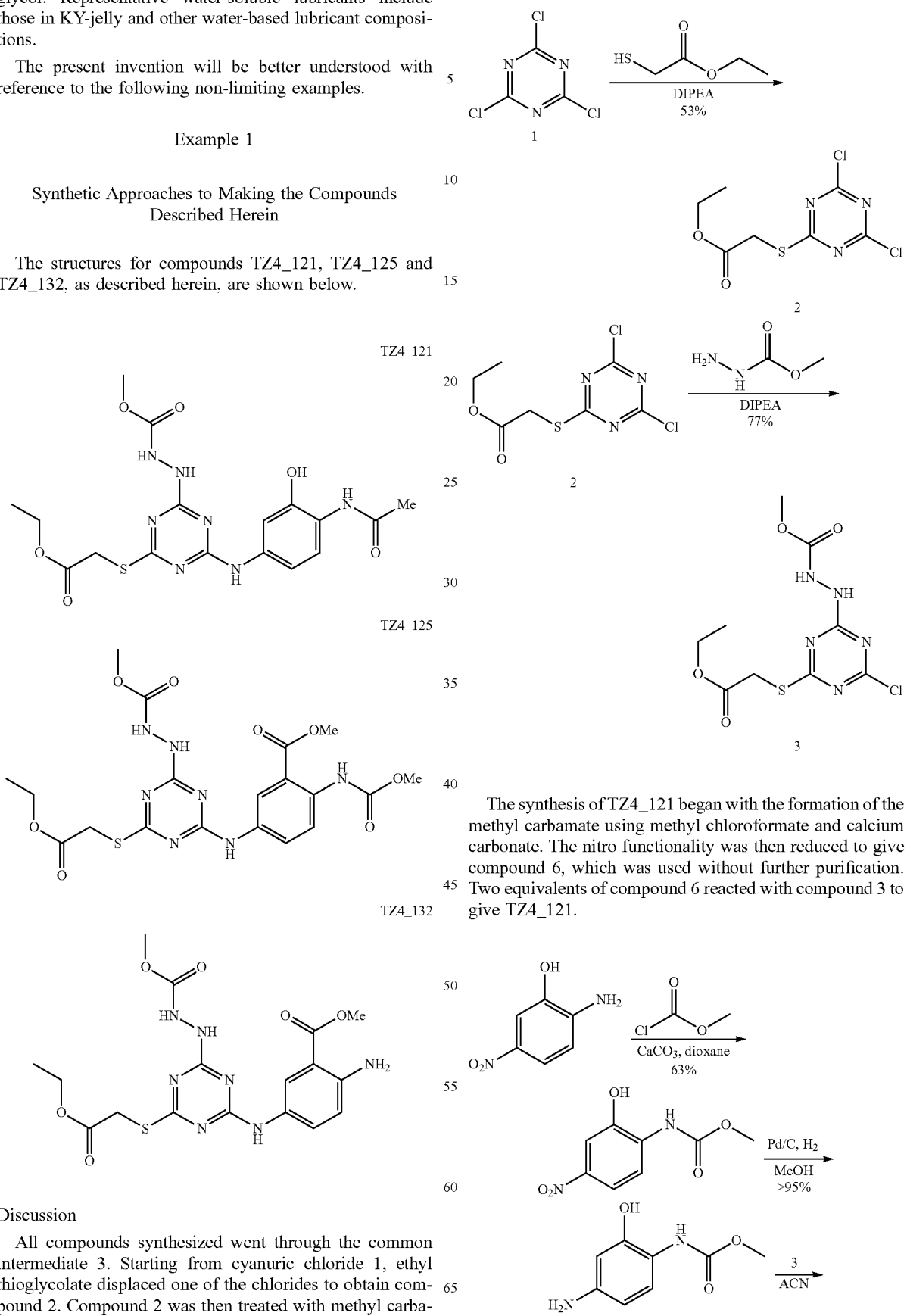

Discussion

All compounds synthesized went through the common intermediate 3. Starting from cyanuric chloride 1, ethyl thioglycolate displaced one of the chlorides to obtain compound 2. Compound 2 was then treated with methyl carbazate to yield compound 3.

The synthesis of TZ4_121 began with the formation of the methyl carbamate using methyl chloroformate and calcium carbonate. The nitro functionality was then reduced to give compound 6, which was used without further purification. Two equivalents of compound 6 reacted with compound 3 to give TZ4_121.

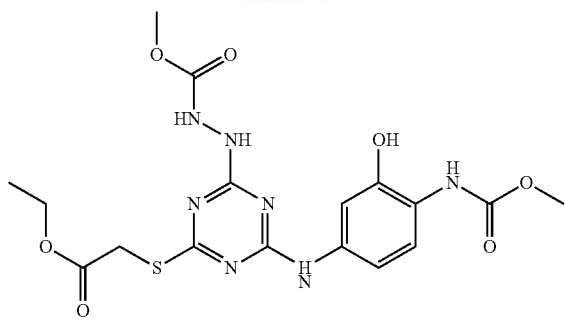

TZ4_121

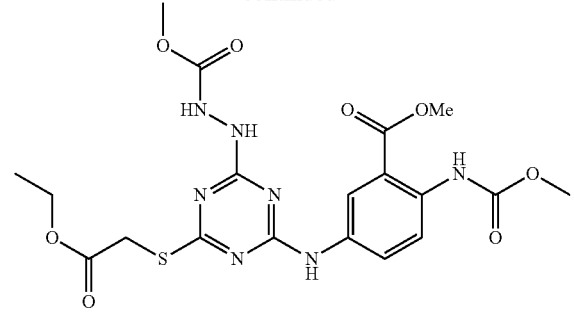

TZ4_125

The synthesis of TZ4_125 began with carboxylic acid 7. The methyl ester was formed in methanol with catalytic sulfuric acid. The methyl carbamate was then introduced in a 2-step, 1-pot approach but treating the aniline with phosgene followed by methanol and 5 Å molecular sieves to give compound 9. The nitro functionality was reduced to give compound 10, which was used without further purification. Compound 10 was reacted with compound 3 in the presence of Hunig's base (DIPEA) to give TZ4_125.

The TZ4_132 began with carboxylic acid 7 which was treated with catalytic sulfuric acid in MeOH to form the methyl ester 8. The nitro functionality was reduced to give compound 11, which was used without further purification. Compound 11 was reacted with compound 3 in the presence of Hunig's base to give TZ4_132.

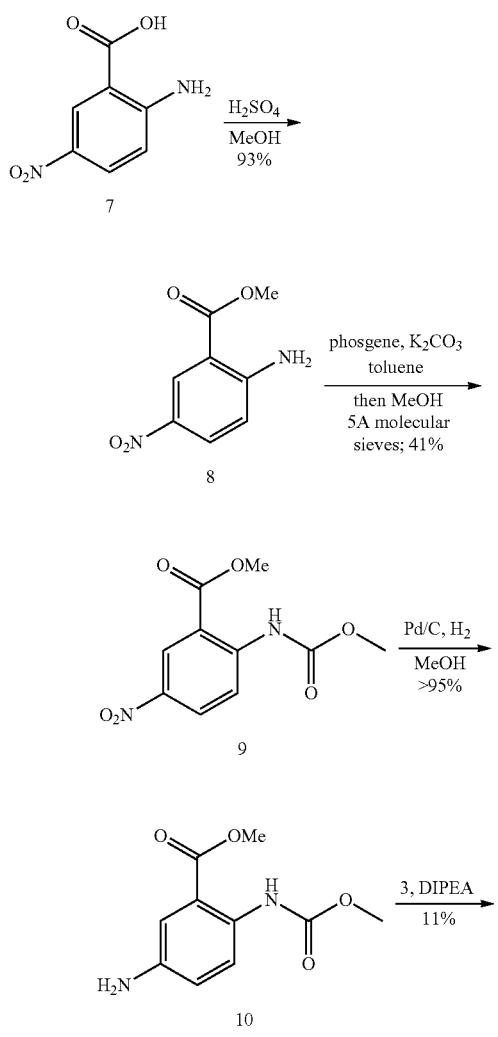

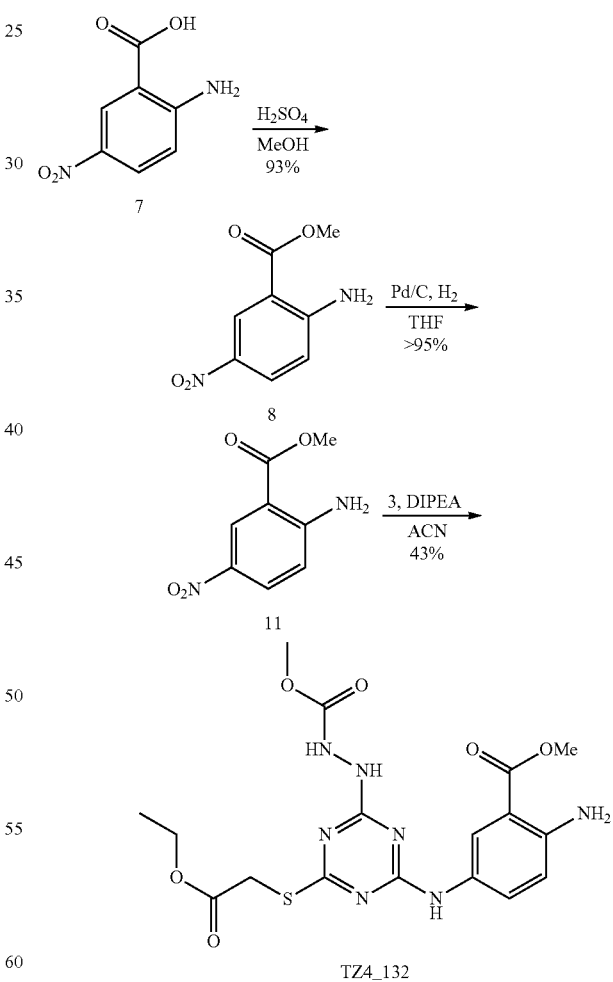

Conclusions:

A number of analogues of the TZ4 series were synthesized and tested for activity. The ready availability of cyanuric chloride allows for a number of analogues to be synthesized by changing the individual "arms" of the molecule. For example, the thiol can be varied with any number of thiols, the carbamate can also be altered to various other amines and the third arm can also be varied to a make an enormous number of analogues.

Experimental:

Analytical Method Details

Analytical HPLC was performed as follows:
Column: Restek Pinnacle II, C18, 5 μm, 150×4.6 mm
Gradient/MP: 5% to 100% eluent B over 25 min (5 minhold)
Total run time: 30 min
Eluent A: $H_2O$+0.1% trifluoroacetic acid
Eluent B: Acetonitrile+0.1% trifluoroacetic acid
Flow: 1.5 mL/min.
Injection volume: 10 uL
Column temperature: Ambient
Detector: 254 nm (VWD)

Compound 2 (338BPAL58):

Cyanuric chloride (5.4 g, 29.2 mmol) and diisopropylethyl amine (8 ml, 46.8 mmol) were combined in tetrahydrofuran (THF) (50 ml) and cooled to 0° C. Ethyl thioglycolate (3.5 g, 29.2 mmol) in THF (10 ml+2×1 ml rinses) was added drop-wise over 30 minutes. The solution was warmed to room temperature and the reaction was complete once room temperature was reached. The solvent was removed. Purification by silica gel chromatography (10% EtOAc/heptane) yielded 4.13 g of pure compound 2. 53% yield.

Compound 3 (333PAL05):

Compound 2 (2.4 g, 9 mmol) was combined with diisopropylethyl amine (1.9 ml) in DCM (50 mL). The reaction mixture was cooled in an ice-water bath and the methyl carbazate (0.822 g, 9.1 mmol) in DCM (20 ml) was added drop-wise. The reaction flask was allowed to warm to room temperature where it was deemed complete by LC/MS. The mixture was poured into water and the organic layer washed with water (3×), dried over $Na_2SO_4$ and concentrated. Purification by silica gel chromatography (20-50% EtOAc in heptane) yielded 2.2 g of pure material. 77% yield.

Compound 5 (336PAL36):

To a solution of compound 4 (1.5 g, 9.7 mmol) in dioxane (30 ml) was added calcium carbonate (0.49 g, 4.9 mmol) followed by methyl chloroformate (1.38 g, 14.6 mmol). The mixture was heated to 80° C. overnight. LC-MS showed the reaction was complete. The solid was filtered and the solvent was evaporated in vacuo. The residue was purified by column chromatography (3-10% MeOH in DCM) to afford 1.3 g of pure material. 63% yield.

Compound 6 (336PAL38):

To a solution of compound 5 (0.06 g, 2.8 mmol) in MeOH (25 ml) was added Pd/C (10%, 0.1 g) and treated with hydrogen (50 psi) for 1 hour. LC-MS showed that the reaction was complete. The solids were filtered and concentrated to give 0.6 g product. The material was used in the next step without further purification.

TZ4_121 (336PAL39):

To a solution of compound 3 (0.1 g, 0.3 mmol) in acetonitrile (10 ml) was added compound 5 (0.113 g, 0.6 mmol). The mixture was stirred at room temperature overnight. LC-MS showed about 83% product was formed. The solvent was evaporated. The crud material was loaded onto an ISCO cartridge and purified by chromatography (4-50% acetone in dichloromethane (DCM)) to afford 125 mg of the product. 86% yield.

Compound 8 (316PAL51):

5-nitroanthranilic acid (1 g, 5.5 mmol) was suspended in MeOH (20 mL) and 0.5 ml of concentrated $H_2SO_4$ was added. Heating was begun and the solids began to dissolve as the temperature reached reflux. The mixture was allowed to heat at reflux for 24 hours, then allowed to cool to room temperature over the weekend. Toluene (20 ml) was added and the bulk of the methanol (MeOH) was boiled off. The solution was heated to 95° C. for 3 hours and concentrated. The material was dissolved in ethyl acetate (EtOAc) and washed with saturated $NaHCO_3$ (3×50 mL) then brine. The organic layer was dried ($Na_2SO_4$), filtered and concentrated to a yellow solid. 1 g. 93% yield.

Compound 9 (338BPAL62):

To aniline 8 (0.2 g, 1.02 mmol) and K2CO3 (0.42 g, 3.06 mmol) in toluene (10 mL) under nitrogen was added phosgene (15% in toluene, 1.5 mL) drop-wise. A yellow precipitate immediately forms. Stirred for 1 hr until the reaction stopped progressing (~50% starting material consumed by TLC). Dry MeOH was added and allowed to stir vigorously for ~15 hours. Diluted with EtOAc (100 ml) and $H_2O$ (100 ml). The organic layer was washed with $H_2O$ (3×), dried over $Na_2SO_4$ and concentrated. The material was purified by column chromatography (15% EtOAc in heptane) to yield 100 mg of product. 41% yield.

Compound 10 (338BPAL63):

Nitro compound 9 (100 mg, 0.42 mmol) was suspended in ethanol (EtOH) (15 ml) with Pd/C (10%, 25 mg). The reaction mixture was hydrogenated for 1.5 hours, when it was deemed complete by TLC. Filtered the catalyst of through Celite and concentrated the filtrate. 90 mg. 100% yield.

TZ4_125 (338BPAL64):

To a solution of compound 3 (115 mg, 0.36 mmol) and diisopropylethyl amine (DIPEA) (741, 0.43 mmol) in acetonitrile (20 ml) at 0° C. was added aniline 10 (82.5 mg, 0.36 mmol) in acetonitrile (8 ml+4 ml rinse) drop-wise over 30 minutes. The ice-water bath was removed and the reaction mixture allowed to warm to room temperature. The material was purified by silica gel chromatography, but still impure. The material form the column was suspended in $Et_2O$ (75 ml) and sonicated. The solids were filtered off and the filtrate was evaporated to a foam. The foam was dissolved in Et2O (5 ml) and pentane (50 ml) was added. The flask was placed in the freezer overnight. The solids were filtered, washed with pentane and dried to yield the desired compound. 19 mg. 11% yield.

Compound 11 (316PAL53):

Compound 8 (1 g, 5.1 mmol) dissolved in THF (50 ml) in a Parr bottle and degassed. Pd/C (10%, 150 mg) was added and the flask purged and filled with hydrogen. Hydrogenated at 40 psi for 24 hours. LC-MS shows the starting material was consumed. The catalyst was filtered off through Celite and washed with MeOH. The filtrate was concentrated to a brown oil. ~1 g. >95% yield.

TZ4_132 (316PAL54):

To compound 3 (250 mg, 0.78 mmol) in ACN (5 ml) was added compound 11 (129 mg, 0.78 mmol) and the contents were stirred until the dissolved. DIPEA (110 mg, 0.86 mmol) in ACN (2 ml) was added and the reaction stirred overnight at room temperature. The reaction was concentrated to a brown oil and then partitioned between EtOAc and water. The organic layer was separated. The aqueous layer was back extracted with EtOAc and the combined organic extracts were washed with 0.1N HCl and brine, dried over $Na_2SO_4$, filtered and concentrated. After trituration with diethyl ether ($Et_2O$), the HPLC purity was only 93%. Purified with an ISCO cartridge (0-5% MeOH in DCM) to obtain a white solid. 150 mg. 43% yield.

Example 2

Analysis of Various Properties of Compound TZ4_121

Compound TZ4_121 was prepared using the synthetic approaches described above, and has the following structure:

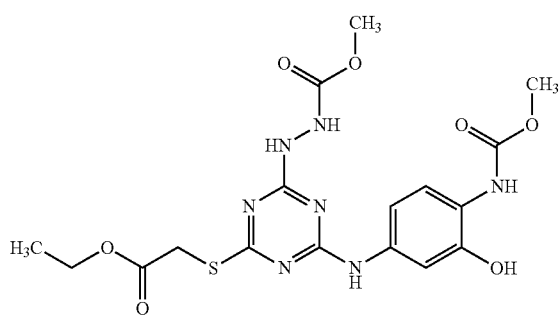 [SMILES: CCOC(=O)CSc1nc(NNC(=O)OC)nc(Nc2ccc(NC(=O)OC)c(O)c2)n1]

Certain physical characteristics of this compound are provided in the table below, and others are provided in FIG. 1.

| | |
|---|---|
| LogP | 2.9 |
| LogD(7.4) | 2.88 |
| mass | 467.456 |
| Polar Surface Area | 211.22 |
| van der Waal's SA | 615.77 |
| Acceptors, Donors | 11.5 |
| pI | 5.54 |

The compound was evaluated using a Principal Component Analysis (PCA) of 15 principal physico-chemical descriptors, and compared to two sub-libraries extracted from eDrugs and DrugBank which define orally bioavailable compounds. This evaluation showed that the compound falls within the same space (characteristics) as other known orally active drugs.

An ADME (adsorption, distribution, metabolism, and excretion) study was performed. It was determined that the compound has the following properties:

1. Good solubility at 100 μM
2. Poor permeability to Caco-2 cells; $0.2 \times 10^{-6}$ cm/sec
3. Recovery high (93%); no non-specific binding
4. Human liver microsomes metabolism $T\frac{1}{2} = 41$ minutes
5. In vitro toxicology; $IC_{50} \sim 2 \times 10^{-5}$ M Additional compounds can be tested using the same protocols:

ADME-Tox: Solution Properties

Aqueous Solubility (Nephelometric Method)

Solutions of the test compound were prepared from DMSO stock solution at the specified test concentrations. The solutions were mixed thoroughly and aliquoted into a 384-well plate, incubated for 1 hour at 37° C., and the degree of light scattering in each solution was measured at 635 nm using a laser-based microplate nephelometer. The mean nephelometric reading at each concentration was calculated and compared to that of the blank solution and a positive control (a solution of latex at a minimum concentration sufficient to give a mean reading higher than that of blank solution, as determined by a calibration curve). The compound was judged to be soluble at a specific concentration if the mean reading was less than the reading of the positive control. In cases where the mean reading was greater than or equal to the positive control, the solution was reported as having a precipitate and a percent precipitation value was calculated using the following formula:

% precipitation=(mean test compound−mean blank)/
(mean positive control−mean blank)×100

In Vitro Absorption

The in vitro absorption was measured using methods described in Hidalgo, I. J. et al. (1989), Gastroenterology, 96: 736-749.

Permeability

The apparent permeability coefficient (Papp) of the test compound was calculated as follows:

$$P_{app}(\text{cm/s}) = \frac{V_R * C_{R,end}}{\Delta t} * \frac{1}{A * (C_{D,mid} - C_{R,mid})}$$

where VR is the volume of the receiver chamber. CR, end is the concentration of the test compound in the receiver chamber at the end time point, Δt is the incubation time and A is the surface area of the cell monolayer. CD, mid is the calculated mid-point concentration of the test compound in the donor side, which is the mean value of the donor concentration at time 0 minute and the donor concentration at the end time point. CR, mid is the mid-point concentration of the test compound in the receiver side, which is one half of the receiver concentration at the end time point. Concentrations of the test compound were expressed as peak areas of the test compound.

Recovery of the Test Compound from the Permeability Assay

The recovery of the test compound was calculated as follows:

$$\text{Recovery}(\%) = \frac{V_D * C_{D,end} + V_R * C_{R,end}}{V_D * C_{D0}} * 100$$

where $V_D$ and $V_R$ are the volumes of the donor and receiver chambers, respectively. CD,end is the concentration of the test compound in the donor sample at the end time point. CR,end is the concentration of the test compound in the receiver sample at the end time point. CD0 is the concentration of the test compound in the donor sample at time zero. Concentrations of the test compound are expressed as peak areas of the test compound.

Fluorescein Assessment for Permeability Assays

Fluorescein was used as the cell monolayer integrity marker. Fluorescein permeability assessment (in the A-B direction at pH 7.4 on both sides) was performed after the permeability assay for the test compound. The cell monolayer that had a fluorescein permeability of less than $1.5 \times 10^{-6}$ cm/s for Caco-2 and MDR1-MDCKII cells and $2.5 \times 10^{-6}$ cm/s for MDCKII cells was considered intact, and the permeability result of the test compound from intact cell monolayer is reported.

ADME-Tox: In Vitro Metabolism

In vitro metabolism was evaluated using the methods described in Obach, R. S. et al. (1997), J. Pharmacol. Exp. Ther., 283: 46-58.

Intrinsic Clearance (microsomes, S9, cryopreserved hepatocytes, recombinant CYP, recombinant UGT) Metabolic stability, expressed as percent of the parent compound remaining, was calculated by comparing the peak area of the compound at the time point relative to that at time-O. The half-life (T½) was estimated from the slope of the initial linear range of the logarithmic curve of compound remaining (%) vs. time, assuming the first-order kinetics. The apparent intrinsic clearance (CLint, in μL/min/pmol, μL/min/mg or μL/min/Mcell) was calculated according to the following formula:

$$CL_{int} = \frac{0.693}{T^{*}_{1/2}\begin{pmatrix}\text{mg protein}/\mu\text{L or million cells}/\mu\text{L or}\\ \text{pmol } CYP \text{ } isoyme/\mu\text{L}\end{pmatrix}}$$

ADME-Tox: In Vitro Toxicity

Cell Viability

The percent of control activity was calculated by comparing the fluorescence reading in the presence of test compound to that in the absence of a test (control) compound. Subsequently, the percent of inhibition was calculated by subtraction of the percent of control value from 100. $IC_{50}$ values were determined by non-linear regression analysis of the concentration-response curves. These parameters are obtained by Hill equation curve fitting. See, for example, Nociari, M. M. et al. (1998), J. Immunol. Meth., 213: 157-167. The results are shown in FIG. 2, which shows that the $IC_{50}$ was around 17 μM.

Example 3

In Silico Assay

The purpose of this example was to determine the minimum sequence on either side of the critical SEMG1 (Gene ID: 6406 as recorded at the NCBI database), residue Cys239 (C11 in peptide), that retains binding to EPPIN and inhibits sperm motility. It was determined that this SEMG1 sequence is E229 to Q247:

(SEQ ID NO: 3)

$E^{1}HS^{3}SKVQ^{7}TS^{9}LC^{11}PAHQDKLQ^{19}$

As a result of this information, a 3D peptide model was constructed, using the approach discussed in Silva et al., Biology of Reproduction, (2012) 87(3):56, 1-8. Briefly, three-dimensional homology models for the EPPIN C-terminal region (K73-P133) were built using the SWISS-MODEL Workspace [Arnold et al., Bioinformatics 2006; 22:195-201; Schwede et al., Nucleic Acids Res 2003; 31:3381-3385; and Bordoli et al., Nat Protocols 2008; 4:1-13.]. After template identification, four templates were chosen (Protein Data Bank identification [PDB ID]) based on the percentage of sequence identity to EPPIN C-terminus: bovine trypsin inhibitor (aprotinin; 1bpiA), boophilin (2odyE), textilinin-1 (3bybB), and alpha3 chain of human type VI collagen (1kthA). EPPIN structural models were then generated using the described templates as reference structures. The quality of the resulting three-dimensional models was compared using QMEAN Z-score (global quality of the generated model) [22]. We selected the model with the highest QMEAN Zscore and then created EPPIN C-terminal model figures using Swiss-PDB Viewer 4.04 (Swiss Institute of Bioinformatics) and rendered with POV-Ray 3.6 (Persistence of Vision Raytracer Pty Ltd).

Using this model, the SEMG1 peptide was docked to EPPIN. The docking results allowed the amino acid residues of EPPIN that bind to this peptide to be mapped. It was determined that EPPIN residues bind specific SEMG1 peptide residues:

| EPPIN Residue | SEMG1 peptide E229-Q247 (1-19) | H-bond |
|---|---|---|
| Y107 | Q7 | 1.863 Å |
| N113 | S3 | 1.918 Å |
| N114 | Q7 | 1.9 A |
| N116 | Q7 | 1.966 Å |
| Q118 | S9 | 2.093 Å |

While not wishing to be bound to a particular theory, it is believed that these EPPIN residues are most likely the critical ones to block in order to inhibit sperm motility. Compound TZ4_121, as described herein, binds to EPPIN residues Y107, N116 and Q118. The information from SEMG1 peptide binding, indicates that an active compound would need to cover a surface area of ~8.9×6.5 Å of the binding site. This relative large size is not unexpected for protein-protein interaction sites.

Example 5

AlphaScreen™ Assay: Epitope Assay Showing Inhibition of Anti-EPPIN Binding to EPPIN In this compound screening assay, histidine-tagged recombinant human EPPIN was attached to NTA-donor beads and anti-EPPIN (S21C; against the EPPIN C-terminal domain) was attached to protein A-acceptor beads. This epitope specific assay gave strong and stable binding between EPPIN and the antibody. For high throughput screening (HTS) of compounds, the AlphaScreen™ assay developed by PerkinElmer (Waltham, Mass.) was adapted. In the AlphaScreen™ (amplified luminescent proximity homogeneous assay) assay donor and acceptor beads (~200 nm) are employed to hold interacting protein molecules. When the interacting protein molecules bind (for example EPPIN {on the donor bead} and anti-EPPIN {on the acceptor bead}), singlet state oxygen molecules diffuse from the donor bead to the acceptor bead (~4 μsec) and fluorophores subsequently emit light at 520-620 nm.

Example 4

Computer Assisted Sperm Assay (CASA) Results

Computer-assisted sperm analysis (CASA) was used as a live cell compound screen for determining the effect of compounds on human sperm motility. Computer-assisted sperm analysis (CASA) was performed using the approach taught in Mitra et al., Biology of Reproduction, Vol. 82, p 491 (2010), to determine the parameters of the control versus compound-treated spermatozoa. The parameters measured are: average pathway velocity (VAP: the average velocity of the smoothed cell path in 1 m/sec), the straight-line velocity (VSL: the average velocity measured in a straight line from the beginning to the end of track in 1 m/sec), the curvilinear velocity (VCL: the average velocity measured over the actual point-to-point track of the cell in 1 m/sec), the lateral head amplitude (ALH: amplitude of lateral head displacement in 1 m), the beat cross-frequency (BCF: frequency of sperm head crossing the sperm average path in Hz), the straightness (STR: the average value of the ratio VSL/VAP in %), and the linearity (LIN: the average value of the ratio VSL/VCL in %). The sperm motility parameters are assessed in pre-warmed (37° C.) two- or four-chambered 20-mm Leja slides, loading 5 μL or 2 μL, respectively, of the samples in each chamber and immediately using CASA. This computerized measuring device included a phase-contrast microscope (Olympus CX41), a camera, a mini-therm stage warmer, an image digitizer, and a computer to store and analyze data. The software used for data analysis is the HTR Ceros 12.3 (Hamilton-Thorne Biosciences). A range of 13 to 20 fields are scanned from each chamber. Progressive cells had to have a minimum of 25 μm/sec VAP and 80% of STR. The parameters of the Hamilton-Thorne Ceros 12.3 are listed in the following table.

Parameters of the Hamilton-Thorne Ceros 12.3

| Parameter Value |
| --- |
| Frame rate (Hz) 60 |
| No. of frames acquired 60 |
| Minimum contrast 80 |
| Minimum size (pixels) 3 |
| Default cell size (pixels) 6 |
| VAP (μm/sec) 25 |
| STR (%) 80 |
| Slow cells Static VAP cut-off (μm/sec) 5 |
| VSL cut-off (μm/sec) 11 |
| Standard objective 10X |
| Chamber depth (μm) 20 |
| Temperature (° C.) 37 |

Figure 3:
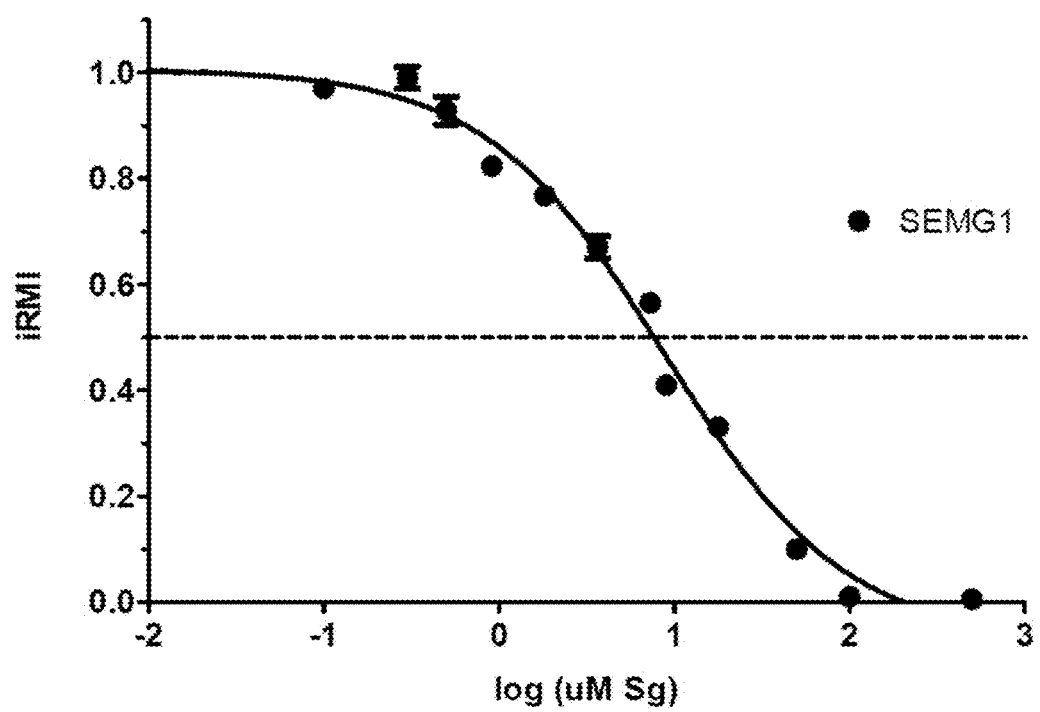
FIGS. 3 and 4 are charts showing IC50 values, as evaluated using a computer aided spermatozoa analysis (CASA), on semenogelin (FIG. 3) and compound TZ4-121 (FIG. 4). The data is shown in terms of log of semenogelin or TZ4_121 concentration (log (µM) vs. RMI (relative motility index).
Figure 4:
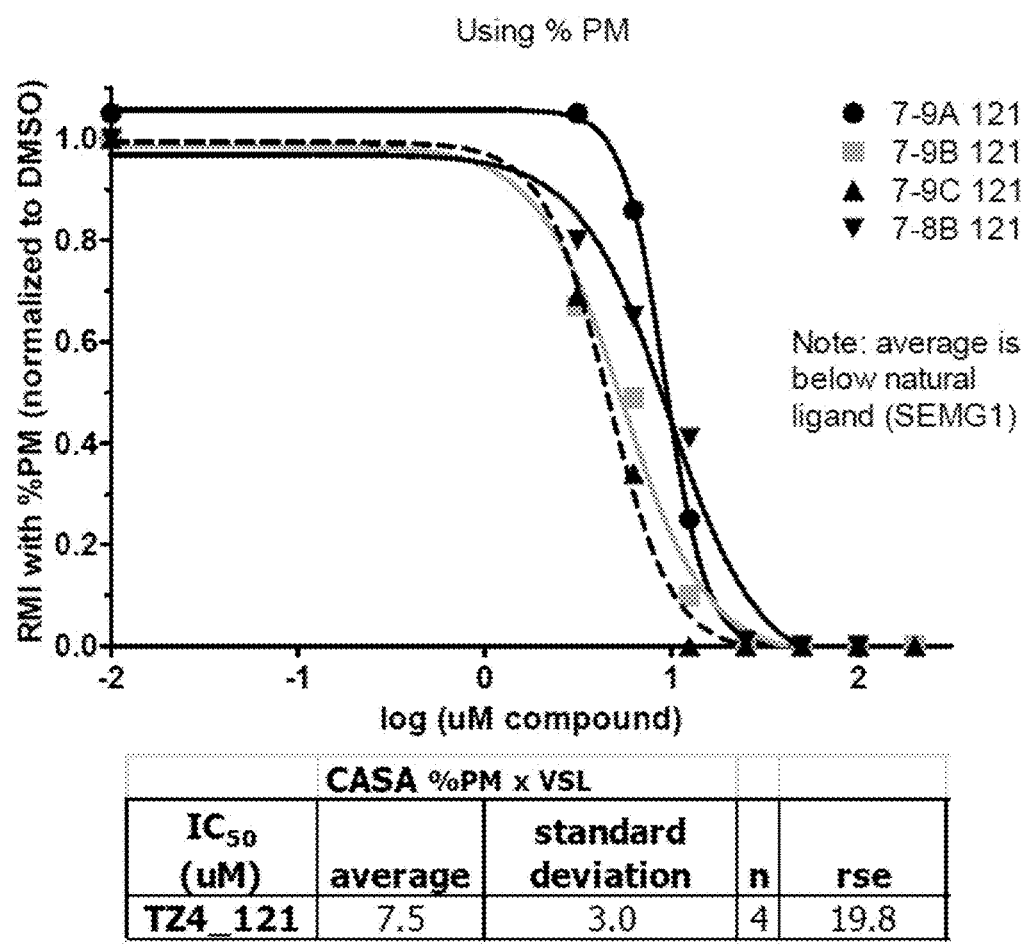

The data on semenogelin and TZ4-121 is shown in FIGS. 3 and 4, respectively. The $IC_{50}$ values for semenogelin (approximately 9 μM) and TZ4-121 (approximately 7.5 μM) are reasonably close, so the activity would be expected to be comparable, with TZ4-121 being slightly more active. In these figures, RMI=relative motility.

To facilitate the $IC_{50}$ evaluation of compounds using different ejaculates, reducing inter-assay variation due to differences in sperm quality in different semen samples, an index of relative motility inhibition (RMI) was developed. This is calculated as: RMI=[% motility*VSL]; percentage of motile sperm (% motility) or the percentage of progressively motile sperm (% progressive motility, RPMI) multiplied by the straight-line velocity (VSL); the average velocity measured in a straight line from the beginning to the end of a sperm track in μm/sec. Normalized RMI (RPMI) was calculated by dividing the RMI of each experimental condition by its respective DMSO control.

Figure 5:
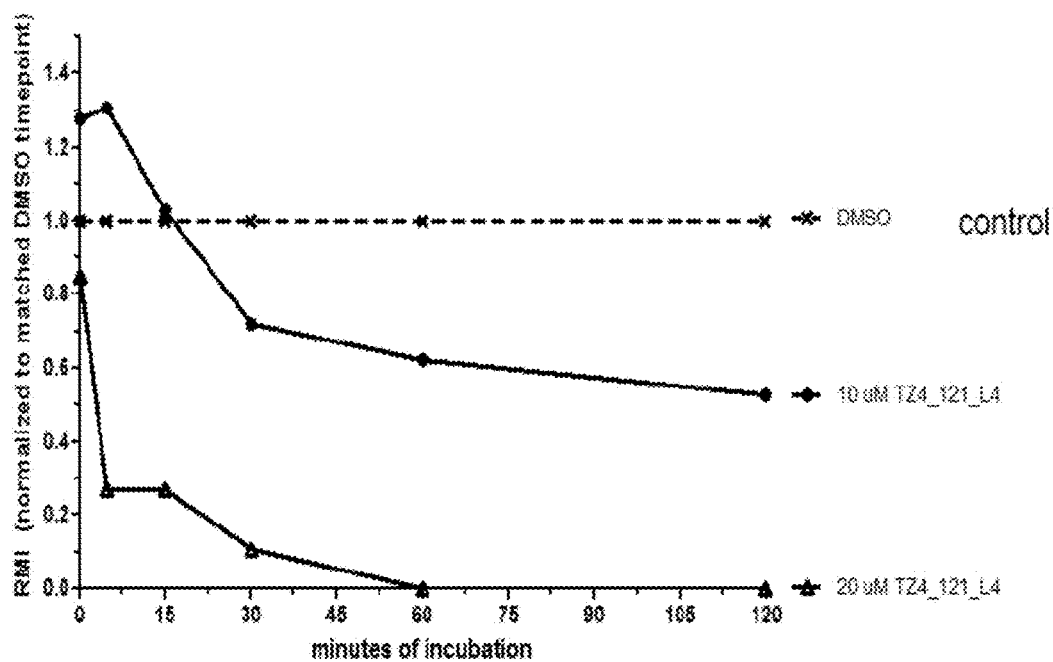
FIG. 5 is a time course study of the effectiveness of TZ4_121 at inhibiting sperm motility, as RMI vs. minutes of incubation. The Xs relate to DMSO (control); circles relate to TZ4_121 at a concentration of 10 µM; triangles relate to TZ4_121 at a concentration of 20 µM.

The time course of sperm motility was evaluated (FIG. 5), and the data showed that TZ4-121, at a concentration of around 20 μM, would likely result in infertility within about 3-5 minutes.

Using this screening assay, one can, in a high-throughput manner, identify compounds effective at inhibiting the binding of EPPIN to semenogelin. This technology has been designed for high throughput screening, and can be adapted for use in 384 well plates to screen compound databases.

Strongly positive hits can be retested in a dilution series, and those compounds which still remain positive can be examined for their aqueous solubility, lipophilicity (ability to go through the cell membrane) and chemical stability. Compounds with the potential for drug development (i.e. solubility, selectivity and potency) will be considered candidates for further drug development, and possible for lead optimization chemistry.

Example 6

Mechanism of Action—Lowering of Internal Sperm pH

A series of experiments was performed to determine the mechanism of action of the compounds described herein. The experiments were carried out as described in O'Rand and Widgren, "Loss of Calcium in Human Spermatozoa via EPPIN, the Semenogelin Receptor," Biology of Reproduction, (2012) 86(2):55, 1-7.

Analysis of Sperm Motility

The analysis of sperm motility was carried out with computer-assisted sperm analysis (CASA) (Ceros version 12.3 software; Hamilton-Thorne), using the techniques taught in Mitra et al., Biology of Reproduction, Vol. 82, p 491 (2010).

Measurement of Intracellular Free Calcium

Fluo-4 AM-loaded spermatozoa were pipetted into 96-well black-walled plates (Perkin Elmer, Waltham, Mass.) at 1.13105-0.93105 spermatozoa/well in 50 μl of M16M at 378 C, and read in a BioTek (Winookski, Vt.) Synergy2 Multiplatform automated plate reader (with heater and shaker). Wells were excited using a 485/20 filter, and emission was read with a 528/20 filter, and data were acquired using a kinetic modification of the Alexafluor 488 protocol in the Gen5 software program (BioTek). Calibration of Fluo-4 in the plates showed that metal-free Fluo-4 had 1/183 the fluorescence of the calcium-saturated complex. After treatment of spermatozoa in each well with control or test reagents was completed (10-15 min), the Fluo-4 in the spermatozoa in each well was calibrated by adding ionomycin (2.5 μM), followed 15 min later by the addition of $Mn^2$ (2 mM $MnCl_2$) to bring the fluorescence (F) to 30% of that of the saturated dye. Fifteen min later, lysis of the spermatozoa with 1% Triton X-100 gave the background signal. Using these values for each well, the Fmax and Fmin were calculated according to the method of Kao et al. [Kao et al., J Biol Chem. 1989; 264:8179-8184.].

Fluorescence measurements were converted to calcium concentration according to the equation $$[Ca^{2+}]=K_d([F-F_{min}]/[F_{max}-F])$$

The Kd (dissociation constant) for Fluo-4=345 nM.

Readings for each well were normalized, averaged, and expressed as percentages. Data from three ejaculate samples are reported.

Dye leakage [12] from Fluo-4-loaded spermatozoa was measured by removing spermatozoa every 15 min (from t=5 to t=65 min) from the incubation medium by centrifugation and measurement of Fluo-4 fluorescence in the supernatant. There was minimal leakage at 15 min and 5% leakage after 1 h incubation.

pH Detection

The AM ester derivative of the pH-sensitive dye BCECF (5 μM; Molecular Probes) was used to detect changes in the pH in spermatozoa treated with SEMG1. Spermatozoa were loaded with BCECF-AM for 30 min in bovine serum albumin-free medium, centrifuged to remove extracellular dye, and resuspended in M16M. Changes to 1.13105-0.93105 spermatozoa/well in 50 μl of M16M at 378 C after treatment with 3.2 μM SEMG1 were monitored in a BioTek (Winookski, Vt.) Synergy2 Multiplatform automated plate reader (with heater and shaker); wells were excited using a 485/20 filter and emission read with a 528/20 filter. Fluorescence was read immediately and recorded every 10 sec; readings for each time point were normalized, averaged, and expressed as percentages of decrease in relative fluorescent units. Data from three ejaculate samples are reported.

Calcium Changes in Spermatozoa Treated with Active Compounds

The contraceptive C-terminal epitope of EPPIN was identified as amino acids 101-125 (TCSMFVYGGCQGNNNNFQSKANCLN) (SEQ ID NO. 1). Affinity purified rabbit antibodies (anti-S21C antibodies) to the EPPIN S21C epitope (SMFVYGGAQGNNNNFQSKANC) (SEQ ID NO. 4) had effects similar to those of recombinant SEMG1, namely, the dose dependent inhibition of the progressive motility of spermatozoa [O'Rand, et al., Biol. Reprod. 2009; 80:279-285]. To determine whether the administration of the compounds described herein result in loss of $[Ca^{2+}]$, spermatozoa loaded with the calcium indicator Fluo-4 can be treated with the compound, for example, at a concentration of 10 µM, in M16-modified medium (M16M), in wells of a single 96-well black-walled plate in the automated plate reader with 150 µg/ml of anti-S21C antibody, and calcium levels can be determined.

Treatment of Human Spermatozoa with Active Compounds

Figure 6:
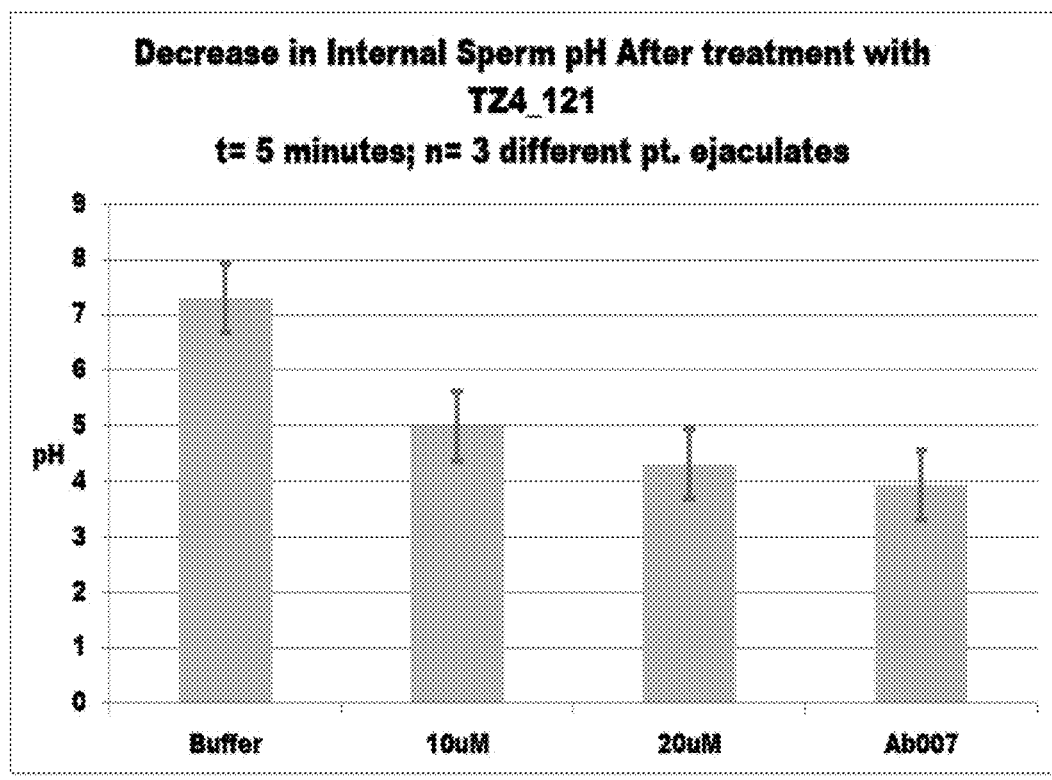
FIG. 6 is a chart showing the decrease in internal sperm pH following treatment with buffer (control), TZ4_121 at 10 and 20 µM, and an anti-EPPIN antibody (Ab007).
Figure 7:
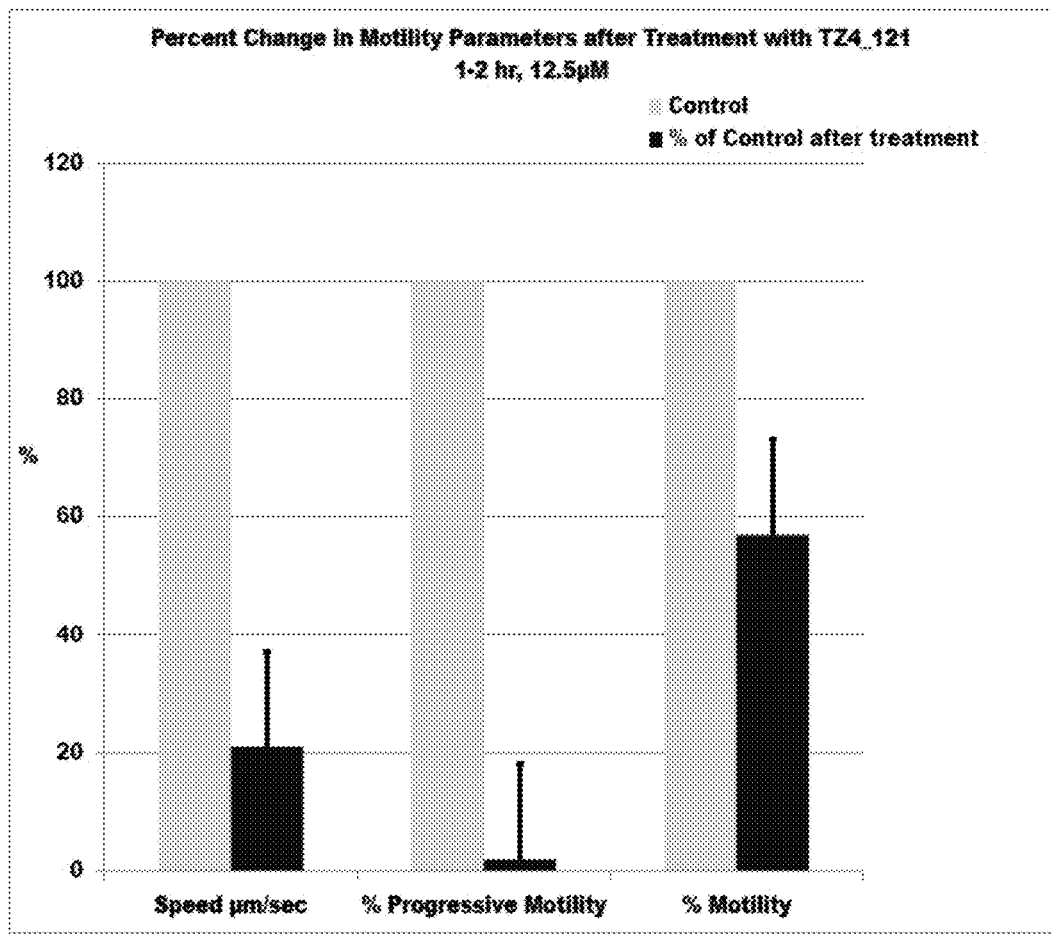
FIG. 7 is a chart showing the change in sperm motility following treatment with TZ4_121 at a concentration of 12.5 µM. In each of the three pairs of columns, the left-most column is control, and the right-most column relates to the percent of control following treatment. The motility is shown in terms of speed (µm/sec), percent progressive motility, and % motility.

Treatment of spermatozoa with TZ4-121 produced a significant loss of calcium, which is accompanied by a significant decrease in pH (FIG. 6) and a significant decrease in progressive motility (FIG. 7). These figures show that the compound acts like semenogelin in that it lowers the pH inside the sperm cell resulting in inhibition of motility.

The results of this study demonstrate that the male contraceptive target EPPIN controls sperm motility in the ejaculate by binding the active compound, resulting in a decrease in pH, and subsequent loss of intracellular calcium. Thus, the active compounds can substitute for SEMG1, and mimic anti-EPPIN binding, providing the basis for a non-antibody, non-hormonal male contraceptive.

Example 7

Docking Results Using Clus Pro 2

ClusPro2 is web based service with an interactive software program from the Structural Bioinformatics Lab at Boston University. A receptor (protein) and a ligand (peptide) can be entered into the program and the best fit of the peptide into the receptor docking site determined. ClusPro2 is described, for example, in Kozakov et al., "How good is automated protein docking? Proteins: Structure, Function, and Bioinformatics," 2013 August; 2159-2166.

SEMG1 Peptide Binding to EPPIN

It was determined that the minimum sequence on either side of the critical SEMG1 residue Cys239 (C11 in peptide) that retains binding to EPPIN and inhibits sperm motility is SEMG1 sequence E229 to Q247: $E^1HS^3SKVQ^7 TS^9LC^{11}$ PAHQDKLQ$^{19}$ (SEQ ID NO. 3).

Figure 8:
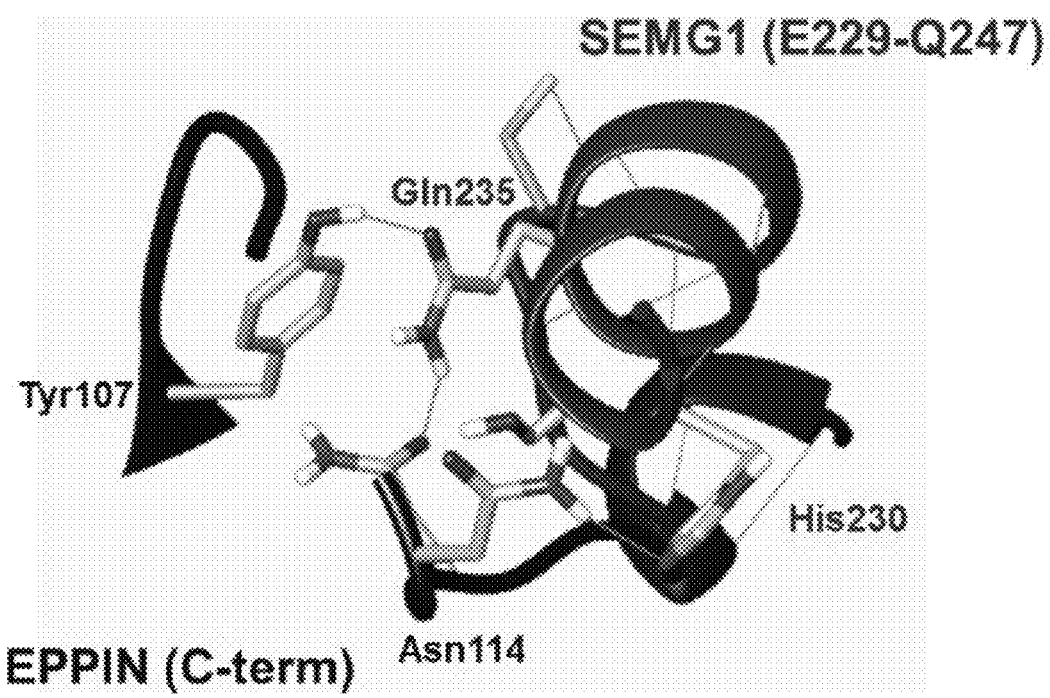
FIG. 8 is an illustration of the binding of amino acids E229-Q247 of semenogelin (SEMG1) to EPPIN. The illustration shows that semenogelin binds to EPPIN at amino acids Y107 and N114 of EPPIN.

This information was used to construct a 3D peptide model and subsequently dock the SEMG1 peptide to EPPIN. This is shown in FIG. 8.

Example 8

Docking Results Using SwissDock

SwissDock, a protein-small molecule docking web service based on EADock DSS, is an interactive software program from the Swiss Institute for Bioinformatics. The structure of a small organic compound and the structure of a protein with a docking site can be entered into the program and the best fit of that compound into the docking site determined.

EPPIN Homology Modeling

Three-dimensional homology models for the EPPIN C-terminal region (K73-P133) were built using the SWISS-MODEL Workspace (Silva et al., Biology of Reproduction (2012) 87(3):56, 1-8). After template identification, four templates were selected (Protein Data Bank identification [PDB ID]) based on the percentage of sequence identity to EPPIN C-terminus: bovine trypsin inhibitor (aprotinin; 1bpiA), boophilin (2odyE), textilinin-1 (3bybB), and alpha3 chain of human type VI collagen (1kthA). EPPIN structural models were then generated using the described templates as reference structures. We compared the quality of the resulting three-dimensional models using QMEAN Z-score (global quality of the generated model) [22]. The model with the highest QMEAN Z-score was selected, and then EPPIN C-terminal model figures were created using Swiss-PDB Viewer 4.04 (Swiss Institute of Bioinformatics) and rendered with POV-Ray 3.6 (Persistence of Vision Ray-tracer Pty Ltd).

Figure 9:
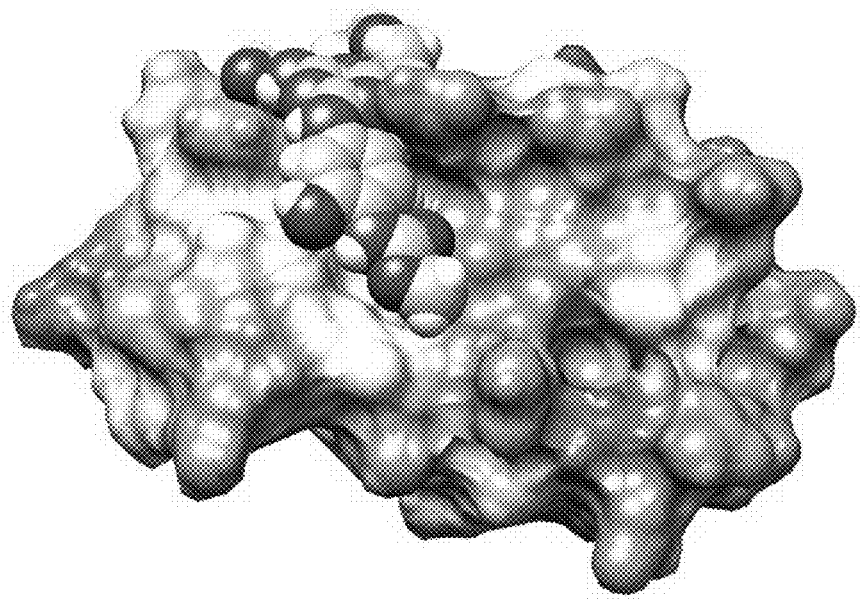
FIG. 9 is an illustration of the docking results for TZ4_121 to the C-terminal portion of EPPIN, using a Swiss-Dock protocol.

Because Clus Pro only works with peptides, and the goal was to evaluate the binding of small molecules to EPPIN, Swiss-Dock was used. The amino acids in the binding site on EPPIN were inputted, and then the chemical formula for TZ4_121 was added, and the software calculated the "best fit" (lowest energy: delta g). Using this approach, the docking of compound TZ4_121 (solid spheres) in the SEMG1 binding site on the surface of EPPIN was evaluated (FIG. 9). The hydrogen bonds between EPPIN and the compound are shown below. (n=3 independent experiments).

Example 9

Results with Metabolites

Figure 10:
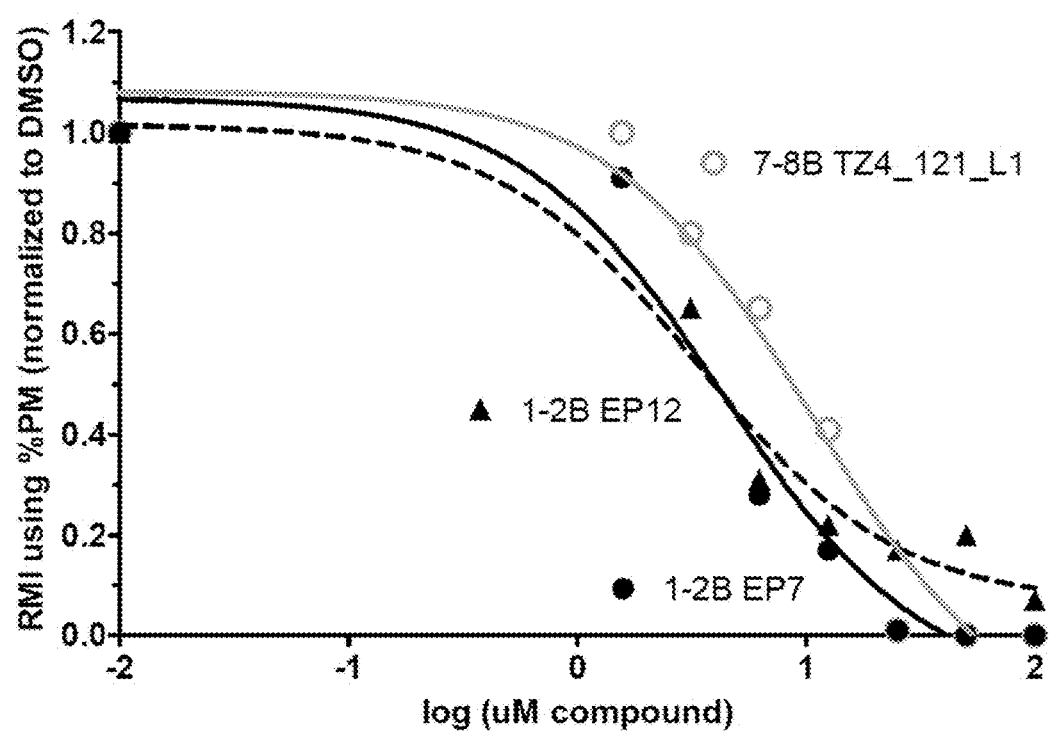
FIG. 10 is a chart showing the change in sperm motility (RMI, using % progressive motility (PM)) following administration of TZ4-121 (referred to in the chart as EP7), EP12, the de-ethylated metabolite of TZ4-121. Open Circles relate to EP7 experiment performed Jul. 7, 2013, and triangles relate to EP12. Closed circles relate to EP7 experiment performed at the same time as EP12.

TZ4_121 includes an ethyl ester moiety. This moiety is metabolized in vivo, so an experiment was performed to compare the effect of TZ4_121 and its de-ethylated metabolite on sperm motility, using the techniques outlined above. The data, shown in FIG. 10, show that the metabolite is slightly more active, with an $IC_{50}$ of around 3.4 µM versus 4.3 µM for the parent compound, in terms of progressive motility.

While the foregoing specification teaches the principles of the present invention, with examples provided for the purpose of illustration, it will be understood that the practice of the invention encompasses all of the usual variations, adaptations and/or modifications as come within the scope of the following claims and their equivalents. All references cited herein are incorporated by reference in their entirety for all purposes.

The invention claimed is:

1. A method of providing contraception, comprising administering an effective amount of a compound having one of the following formulas:

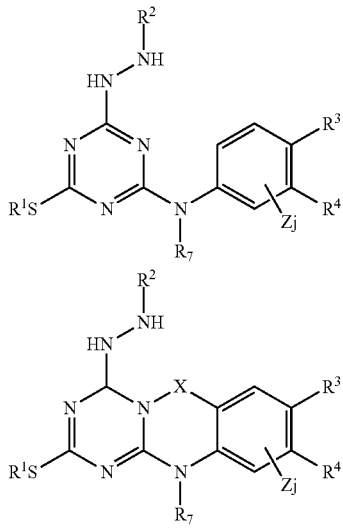

and tautomers, and pharmaceutically-acceptable salts thereof,
wherein:
$R^1$ is —CH$_2$R$^5$,
$R^2$ is H, C$_{1-8}$ alkyl, C$_{1-8}$ haloalkyl, C$_{2-8}$ alkenyl, C$_{2-8}$ alkynyl, aryl, arylalkyl, alkylaryl, C(X)R$^6$ or C(X)XR$^6$,
$R^3$ is —NHR$^7$, —C(X)NHR$^7$, —NHC(X)R$^7$, —NHC(X)XR$^7$, —R$^8$, or C(X)R$^8$;
$R^4$ is OR$^7$ or —C(X)OR$^7$,
$R^5$ is H, F, C$_{1-8}$ alkyl, C$_{1-8}$ haloalkyl, C$_{2-8}$ alkenyl, C$_{2-8}$ alkynyl, aryl, arylalkyl, alkylaryl, —XC(X)XR$^6$, C(X)XR$^6$, or C(X)R$^6$,
$R^6$ and $R^7$ are H, C$_{1-8}$ alkyl, C$_{1-8}$ haloalkyl, C$_{2-8}$ alkenyl, C$_{2-8}$ alkynyl, aryl, arylalkyl, or alkylaryl;
$R^8$ is

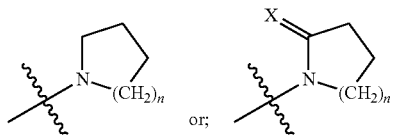

X is O, S, or NR$^7$,
Y is O, S, NR$^7$, or C(R$^7$)$_2$,
Zj refers to j number of Z substituents, which substituents can be present at any carbon atom on the benzene ring, wherein j is 0, 1 or 2, each Z is, individually, a substituent species selected from the group consisting of C$_{1-8}$ alkyl, C$_{1-8}$ substituted alkyl, C$_{2-8}$ alkenyl, C$_{2-8}$ substituted alkenyl, C$_{3-8}$ cycloalkyl, C$_{3-8}$ substituted cycloalkyl, aryl, substituted aryl, alkylaryl, substituted alkylaryl, arylalkyl, substituted arylalkyl, halo, —OR$^7$, —N(R$^7$)$_2$, —CF$_3$, —CN, —NO$_2$, —C$_2$R$^7$, —SR$^7$, —N$_3$, —C(=O)N(R$^7$)$_2$, —NR$^7$C(=O)R$^7$, —C(=O)R$^7$, —C(=O)OR$^7$, —OC(=O)R$^7$, —O(CR$^6$R$^7$)$_r$C(=O)R$^7$—, —O(CR$^6$R$^7$)$_r$NR$^7$C(=O)R$^7$, —O(CR$^6$R$^7$)$_r$NR$^7$SO$_2$R$^7$, —OC(=O)NR$^6$R$^7$, —NR$^7$C(=O)OR$^7$, —SO$_2$R$^7$, —SO$_2$NR$^6$R$^7$, and —NR$^7$SO$_2$R$^7$,
r is an integer from 1 to 6, and
n is 0, 1, 2, or 3,
the term "substituted" as applied to alkyl, aryl, cycloalkyl and the like refers to the substituents described above, starting with halo and ending with —NR$^7$SO$_2$R$^7$;
and tautomers, and pharmaceutically-acceptable salts thereof,
wherein the compounds can exist as single stereoisomers or as mixtures of stereoisomers.

2. The method of claim 1, wherein haloalkyl is monofluoromethyl.

3. The method of claim 1, wherein R$^5$ is F, —XC(X)XR—, or C(X)XR$^6$.

4. The method of claim 1, wherein one or more C=X moieties are carbonyl (C=O).

5. A method of providing contraception, comprising an effective amount of a compound having one of the following formulas:

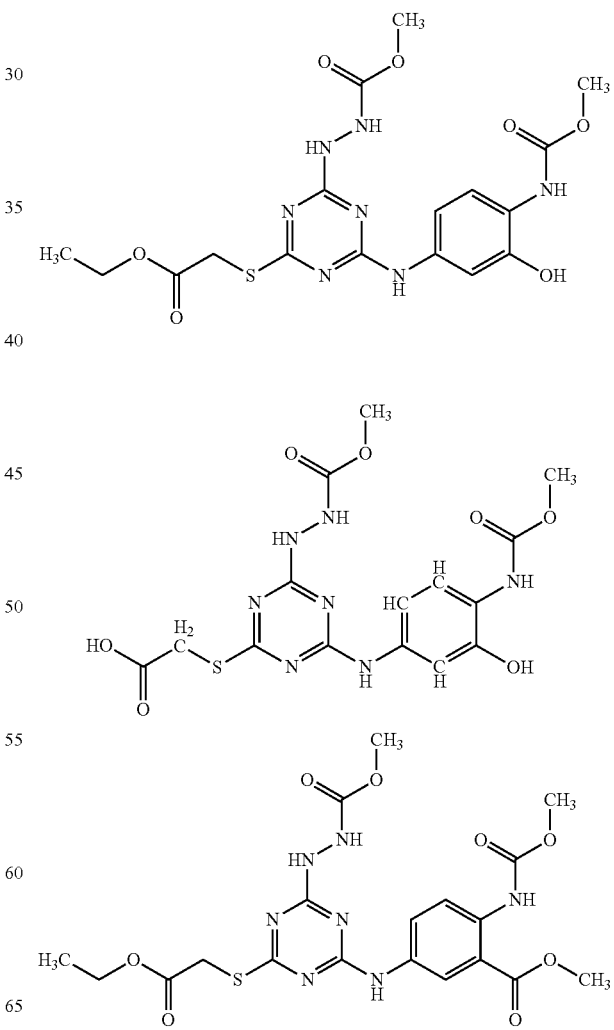

6. A pharmaceutical composition for providing male contraception, comprising an effective amount of a compound of claim 1.

7. The composition of claim 6, further comprising a water-soluble lubricant.

8. A compound having one of the following formulas:

and tautomers, and pharmaceutically-acceptable salts thereof, wherein:

$R^1$ is —$CH_2R^5$, $R^2$ is H, $C_{1-8}$ alkyl, $C_{1-8}$ haloalkyl, $C_{2-8}$ alkenyl, $C_{2-8}$ alkynyl, aryl, arylalkyl, alkylaryl, C(X)$R^6$ or C(X)X$R^6$, $R^3$ is —NH$R^7$, —C(X)NH$R^7$, —NHC(X)$R^7$, —NHC(X)X$R^7$, —$R^8$, or C(X)$R^8$;

$R^4$ is OR' or —C(X)O$R^7$, $R^5$ is H, F, $C_{1-8}$ alkyl, $C_{1-8}$ haloalkyl, $C_{2-8}$ alkenyl, $C_{2-8}$ alkynyl, aryl, arylalkyl, alkylaryl, —XC(X)X$R^6$, C(X)X$R^6$, or C(X)$R^6$, $R^6$ and $R^7$ are H, $C_{1-8}$ alkyl, $C_{1-8}$ haloalkyl, $C_{2-8}$ alkenyl, $C_{2-8}$ alkynyl, aryl, arylalkyl, or alkylaryl;

R⁸ is

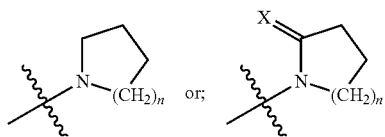

X is O, S, or NR⁷,

Y is O, S, NR', or C(R⁷)₂,

Zj refers to j number of Z substituents, which substituents can be present at any carbon atom on the benzene ring, wherein j is 0, 1 or 2, each Z is, individually, a substituent species selected from the group consisting of $C_{1-8}$ alkyl, $C_{1-8}$ substituted alkyl, $C_{2-8}$ alkenyl, aryl, alkylaryl, arylalkyl, halo, —OR⁷, —N(R⁷)₂, —CF₃, —CN, —NO₂, —C₂R⁷, —SR⁷, —N₃, —C(=O)N(R⁷)₂, —NR⁷C(=O)R⁷, —C(=O)R⁷, —C(=O)OR⁷, —OC(=O)R⁷, —O(CR⁶R⁷)ᵣC(=O)R⁷—, —O(CR⁶R⁷)ᵣNR⁷C(=O)R⁷, —O(CR⁶R⁷)ᵣNR⁷SO₂R⁷, —OC(=O)NR⁶R⁷, —NR⁷C(=O)OR⁷, —SO₂R⁷, —SO₂NR⁶R⁷, and —NR⁷SO₂R⁷, r is an integer from 1 to 6, and n is 0, 1, 2, or 3, and tautomers, and pharmaceutically-acceptable salts thereof, wherein the compounds can exist as single stereoisomers or as mixtures of stereoisomers.

9. The compound of claim 8, wherein haloalkyl is monofluoromethyl.

10. The compound of claim 8, wherein R⁵ is F, —XC(X)XR₆, or C(X)XR₆.

11. The compound of claim 8, wherein one or more C=X moieties are carbonyl (C=O).

12. A compound of claim 8, wherein the compound has the formula:

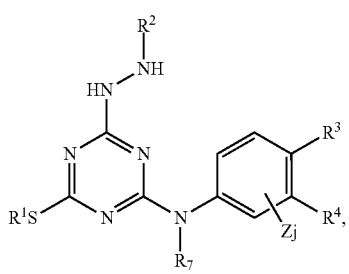

or a pharmaceutically acceptable salt, or tautomer thereof.

13. A compound of claim 8, having one of the following formulas:

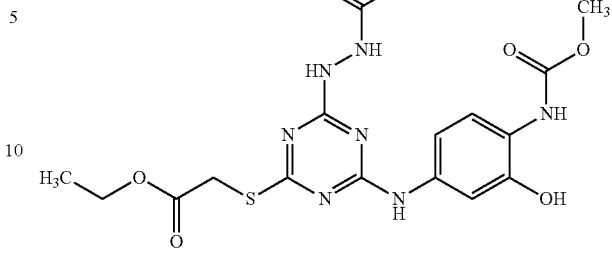

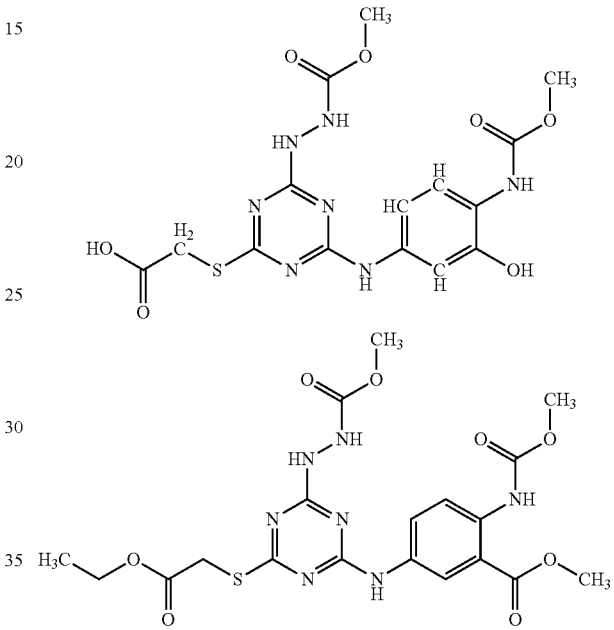

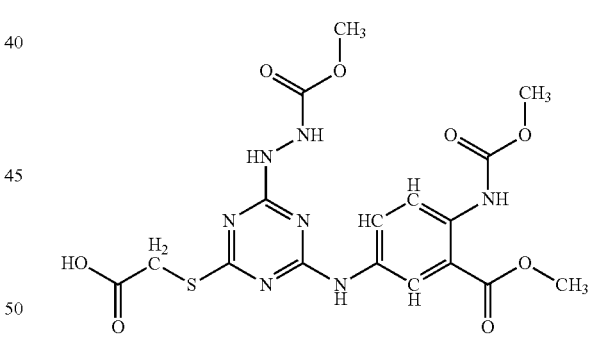

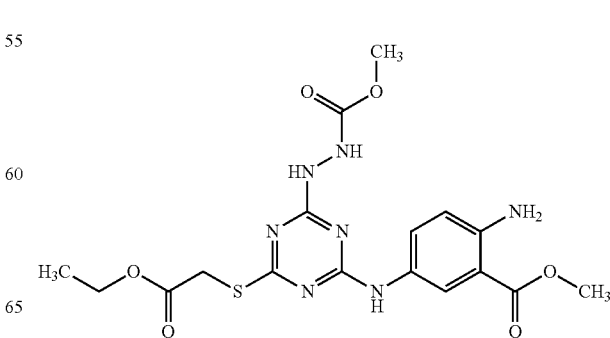

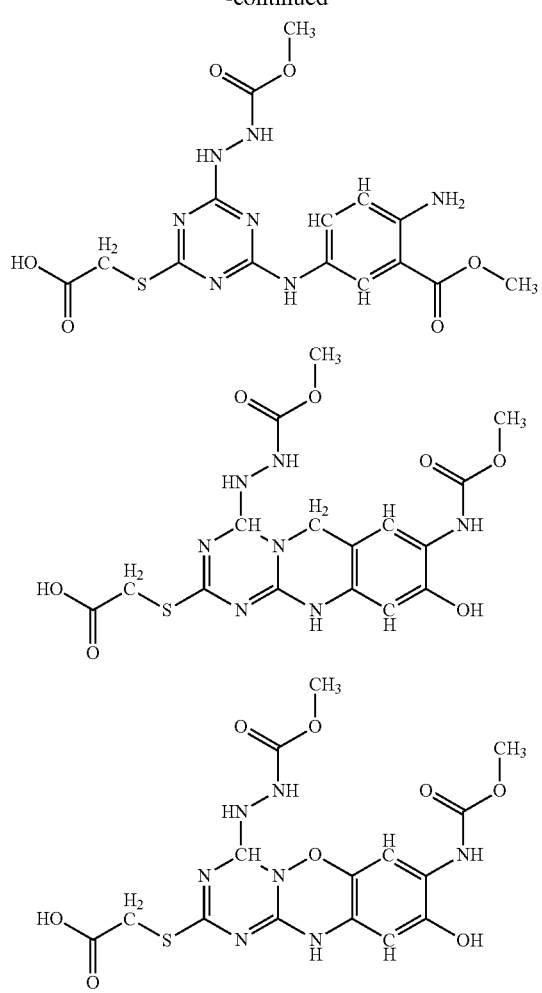
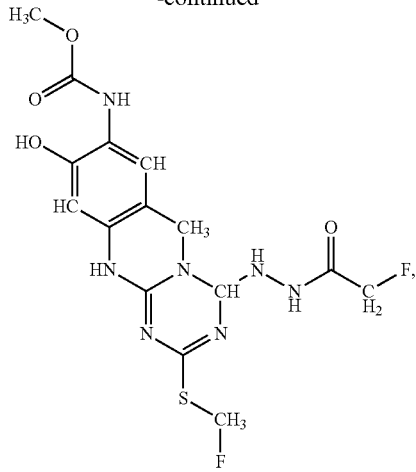
and
or a pharmaceutically acceptable salt, or tautomer thereof.
14. A compound of claim 8, having the formula:
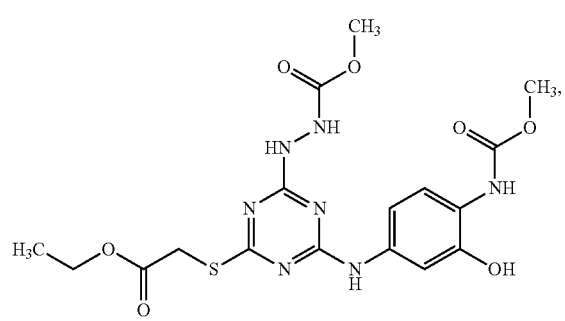 [SMILES: CCOC(=O)CSc1nc(NNC(=O)OC)nc(Nc2ccc(NC(=O)OC)c(O)c2)n1]
or a pharmaceutically acceptable salt, or tautomer thereof.
* * * * *

SEQUENCE LISTING

<160> NUMBER OF SEQ ID NOS: 4

<210> SEQ ID NO 1
<211> LENGTH: 24
<212> TYPE: PRT
<213> ORGANISM: Human

<400> SEQUENCE: 1

Thr Cys Ser Met Phe Val Tyr Gly Gly Cys Gln Gly Asn Asn Asn Asn
1               5                   10                  15

Phe Gln Lys Ala Asn Cys Leu Asn
            20

<210> SEQ ID NO 2
<211> LENGTH: 461
<212> TYPE: PRT
<213> ORGANISM: Human

<400> SEQUENCE: 2

Met Lys Pro Asn Ile Ile Phe Val Leu Ser Leu Leu Ile Leu Glu
1               5                   10                  15

Lys Gln Ala Ala Val Met Gly Gln Gly Gly Ser Lys Gly Arg Leu
            20                  25                  30

Pro Ser Glu Phe Ser Gln Phe Pro His Gly Gln Lys Gly Gln His Tyr
            35                  40                  45

Ser Gly Gln Lys Gly Lys Gln Gln Thr Glu Ser Lys Gly Ser Phe Ser
        50                  55                  60

Ile Gln Tyr Thr Tyr His Val Asp Ala Asn Asp His Asp Gln Ser Arg
65                  70                  75                  80

Lys Ser Gln Gln Tyr Asp Leu Asn Ala Leu His Lys Thr Thr Lys Ser
                85                  90                  95

Gln Arg His Leu Gly Gly Ser Gln Gln Leu Leu His Asn Lys Gln Glu
            100                 105                 110

Gly Arg Asp His Asp Lys Ser Lys Gly His Phe His Arg Val Val Ile
        115                 120                 125

His His Lys Gly Gly Lys Ala His Arg Gly Thr Gln Asn Pro Ser Gln
    130                 135                 140

Asp Gln Gly Asn Ser Pro Ser Gly Lys Gly Ile Ser Ser Gln Tyr Ser
145                 150                 155                 160

Asn Thr Glu Glu Arg Leu Trp Val His Gly Leu Ser Lys Glu Gln Thr
                165                 170                 175

Ser Val Ser Gly Ala Gln Lys Gly Arg Lys Gln Gly Gly Ser Gln Ser
            180                 185                 190

Ser Tyr Val Leu Gln Thr Glu Glu Leu Val Ala Asn Lys Gln Gln Arg
        195                 200                 205

Glu Thr Lys Asn Ser His Gln Asn Lys Gly His Tyr Gln Asn Val Val
    210                 215                 220

Glu Val Arg Glu Glu His Ser Ser Lys Val Gln Thr Ser Leu Cys Pro
225                 230                 235                 240

Ala His Gln Asp Lys Leu Gln His Gly Ser Asp Ile Phe Ser Thr Gln
                245                 250                 255

Asp Glu Leu Leu Val Tyr Asn Lys Asn Gln His Gln Thr Lys Asn Leu
            260                 265                 270

Asn Gln Asp Gln Gln His Gly Arg Lys Ala Asn Lys Ile Ser Tyr Gln
        275                 280                 285

Ser Ser Ser Thr Glu Glu Arg Arg Leu His Tyr Gly Glu Asn Gly Val

```
                290                 295                 300

Gln Lys Asp Val Ser Gln Ser Ser Ile Tyr Ser Gln Thr Glu Lys
305                 310                 315                 320

Ala Gln Gly Lys Ser Gln Lys Gln Ile Thr Ile Pro Ser Gln Glu Gln
                325                 330                 335

Glu His Ser Gln Lys Ala Asn Lys Ile Ser Tyr Gln Ser Ser Ser Thr
                340                 345                 350

Glu Glu Arg Arg Leu His Tyr Gly Glu Asn Gly Val Gln Lys Asp Val
                355                 360                 365

Ser Gln Arg Ser Ile Tyr Ser Gln Thr Glu Lys Leu Val Ala Gly Lys
                370                 375                 380

Ser Gln Ile Gln Ala Pro Asn Pro Lys Gln Glu Pro Trp His Gly Glu
385                 390                 395                 400

Asn Ala Lys Gly Glu Ser Gly Gln Ser Thr Asn Arg Glu Gln Asp Leu
                405                 410                 415

Leu Ser His Glu Gln Lys Gly Arg His Gln His Gly Ser His Gly Gly
                420                 425                 430

Leu Asp Ile Val Ile Ile Glu Gln Glu Asp Asp Ser Asp Arg His Leu
                435                 440                 445

Ala Gln His Leu Asn Asn Asp Arg Asn Pro Leu Phe Thr
                450                 455                 460

<210> SEQ ID NO 3
<211> LENGTH: 19
<212> TYPE: PRT
<213> ORGANISM: Human

<400> SEQUENCE: 3

Glu His Ser Ser Lys Val Gln Thr Ser Leu Cys Pro Ala His Gln Asp
1               5                   10                  15

Lys Leu Gln

<210> SEQ ID NO 4
<211> LENGTH: 21
<212> TYPE: PRT
<213> ORGANISM: Human

<400> SEQUENCE: 4

Ser Met Phe Val Tyr Gly Gly Ala Gln Gly Asn Asn Asn Phe Gln
1               5                   10                  15

Ser Lys Ala Asn Cys
                20
```